United States Patent [19]

Föry et al.

[11] Patent Number: 5,532,203

[45] Date of Patent: Jul. 2, 1996

[54] SELECTIVE SAFENED HERBICIDAL COMPOSITION

[75] Inventors: Werner Föry, Riehen, Switzerland; Elmar Kerber, Görwihl, Germany; Manfred Hudetz, Rheinfelden, Switzerland

[73] Assignee: Ciba-Geigy Corporation, Tarrytown, N.Y.

[21] Appl. No.: 434,902

[22] Filed: May 1, 1995

Related U.S. Application Data

[63] Continuation of Ser. No. 291,319, Aug. 16, 1994, abandoned, which is a continuation of Ser. No. 157,870, Nov. 24, 1993, abandoned.

[30] Foreign Application Priority Data

| Dec. 2, 1992 | [CH] | Switzerland | 3697/92 |
| Jan. 25, 1993 | [CH] | Switzerland | 213/93 |
| Feb. 10, 1993 | [CH] | Switzerland | 397/93 |
| Mar. 25, 1993 | [CH] | Switzerland | 906/93 |

[51] Int. Cl.$^6$ .......................... A01N 25/32; A01N 47/36; C07D 239/47; C07D 239/52

[52] U.S. Cl. .......................... 504/105; 504/106; 504/107; 504/108; 504/109; 504/110; 504/111; 504/112; 504/215; 540/601; 544/63; 544/96; 544/123; 544/320; 544/321

[58] Field of Search .................... 504/112, 215, 504/279, 105, 106, 107, 108, 109, 110, 111; 544/63, 96, 123, 320, 321; 540/601

[56] References Cited

U.S. PATENT DOCUMENTS

| 3,732,223 | 5/1973 | Von Gizycki | 260/249.8 |
| 3,919,228 | 11/1975 | Von Gizycki et al. | 260/256.4 |
| 4,579,583 | 4/1986 | Föry et al. | 71/92 |
| 4,664,695 | 5/1987 | Schurter et al. | 71/92 |
| 5,215,570 | 6/1993 | Burckhardt et al. | 504/104 |
| 5,221,315 | 6/1993 | Föry et al. | 504/178 |

FOREIGN PATENT DOCUMENTS

| 1243674 | 10/1988 | Canada. |
| 2089464 | 8/1993 | Canada. |
| 103543 | 4/1983 | European Pat. Off.. |
| 101670 | 2/1984 | European Pat. Off.. |
| 314505 | 5/1989 | European Pat. Off.. |
| 365484 | 4/1990 | European Pat. Off.. |
| 459949 | 12/1991 | European Pat. Off.. |
| 0492367 | 7/1992 | European Pat. Off.. |
| 555770 | 8/1993 | European Pat. Off.. |
| 4000503 | 7/1991 | Germany. |
| 9216522 | 10/1992 | WIPO. |
| 9317016 | 9/1993 | WIPO. |

OTHER PUBLICATIONS

Chem. Abst. 117;126460c; Baver, et al (corresponds to publication 1) 1992.
P. Pratesi "IL Farmaco Ediyiones Scientifica" vol. XII N. 1 Gennaio 19 57.
Chem. abst. CA 101(5);384804 of EP 101,670 1984.
Chem. Abst. CA 93;419265 of EP 555,770 1993.

*Primary Examiner*—S. Mark Clardy
*Attorney, Agent, or Firm*—George R. Dohmann; Marla J. Mathias; William A. Teoli, Jr.

[57] ABSTRACT

Mixtures of a herbicidally effective amount of a pyridylsulfonylurea of formula I, $$R-\underset{N}{\underset{|}{\bigcirc}}^{A}-SO_2NH-\overset{O}{\overset{||}{C}}-\underset{|}{\overset{R_1}{N}}-\underset{N}{\overset{R_2}{\bigcirc}}-OCH_3 \quad (I)$$

wherein R, $R_1$, $R_2$ and A are as defined in claim 1, and of a herbicide-antagonistically effective amount of a sulfamoylphenylurea of formula II, $$\underset{R_8}{\overset{R_7}{\diagdown}}N-CO-\underset{R_9}{\overset{|}{N}}-\underset{R_{11}}{\overset{R_{10}}{\bigcirc}}-SO_2-NH-CO-A_2, \quad (II)$$

wherein $R_7$ to $R_{11}$ and $A_2$ are as defined in claim 1, are very suitable for controlling weeds in crops of useful plants, especially maize and sugar cane.

23 Claims, No Drawings

SELECTIVE SAFENED HERBICIDAL COMPOSITION

This is a continuation of Ser. No. 291,319, filed Aug. 16, 1994, abandoned, which is a continuation of Ser. No. 157,870, filed Nov. 24, 1993, abandoned.

The present invention relates to a selective herbicidal composition for controlling grasses and weeds in crops of useful plants, especially in crops of maize and sugar cane, which composition comprises a herbicide and a safener (counter-agent, antidote) which protects the useful plants, but not the weeds, against the phytotoxic action of the herbicide, and to the use of that composition or the combination of herbicide and safener in the control of weeds in crops of useful plants.

When using herbicides, the cultivated plants may suffer considerable damage, depending on such factors as, for example, the amount of herbicide and the method of application, the species of cultivated plant, the nature of the soil and climatic conditions, such as, for example, hours of daylight, temperature and amounts of rainfall. Severe damage may occur especially when, in the course of crop rotation, cultivated plants that are resistant to the herbicides are followed by other cultivated plants that have no, or only insufficient, resistance to the herbicides.

In order to deal with that problem, several substances have already been proposed that are capable of specifically antagonising the harmful effect of the herbicide on the cultivated plant, that is to say, are capable of protecting the cultivated plant without having any appreciable influence on the herbicidal action on the weeds to be controlled. It has been found that the proposed safeners often exhibit a very species- or type-specific action both with respect to the cultivated plants and with respect to the herbicide, and in some cases also in dependence on the method of application, that is to say, a specific safener is often suitable only for a specific cultivated plant and a specific class of herbicidal substance.

For example, sulfamoylphenylureas known from EP-A-0 365 484 are suitable for protecting cultivated plants against the phytotoxic action of a very specific class of pyridylsulfonylurea herbicides.

Accordingly, a selective herbicidal composition is proposed according to the invention which comprises as active component, together with inert carriers and adjuvants, a mixture of a) a herbicidally effective amount of a pyridylsulfonylurea of formula I

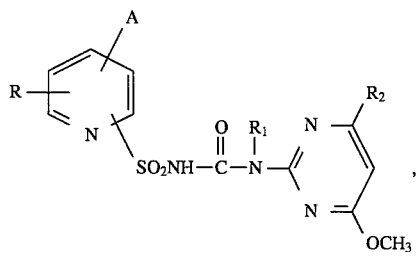

wherein R is hydrogen, halogen, $C_1$–$C_4$alkyl, $C_1$–$C_4$alkoxy or $C_1$–$C_4$alkylthio, or is $C_1$–$C_4$alkyl mono- or poly-substituted by halogen; $R_1$ is hydrogen or methyl; $R_2$ is methyl or methoxy; A is —X—$R_3$ or —N—($R_4$)$R_5$; $R_3$ is $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_3$–$C_6$cycloalkyl, which may for its part be interrupted by oxygen; or is $C_3$–$C_6$alkenyl, or $C_3$–$C_6$alkenyl that is mono- or poly-substituted by halogen, $C_1$–$C_6$alkoxy, $C_3$–$C_6$alkenyloxy or by $C_3$–$C_6$alkynyloxy; or is $C_4$–$C_6$cycloalkyl, or $C_4$–$C_6$cycloalkyl that is mono- or poly-substituted by halogen or by $C_1$–$C_6$alkoxy; or is $C_3$–$C_6$cycloalkyl that is interrupted by oxygen; or is $C_3$–$C_6$alkynyl; X is oxygen or S(O)$_n$; n is 0, 1 or 2; $R_4$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio; $R_5$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio, or is C(O)$R_6$; and $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen; or is phenyl, benzyl, naphthyl or $OR_{12}$, or phenyl, benzyl or naphthyl each substituted by halogen, $C_1$–$C_4$alkyl, $C_1$–$C_4$haloalkyl, $C_1$–$C_4$alkoxy, $C_1$–$C_4$haloalkoxy, $C_3$–$C_6$alkenyloxy, $C_3$–$C_6$alkynyloxy nitro, cyano, $COOR_{13}$, $NR_{15}R_{16}$, $C(O)NR_{17}R_{18}$, $X_1R_{20}$, $SO_2NR_{21}R_{22}$ or by $X_2R_{23}$; $R_{12}$ is $C_1$–$C_6$alkyl, $C_1$–$C_6$haloalkyl, oxetan-3-yl, or $C_4$–$C_6$cycloalkyl, which may for its part be substituted by halogen, $C_1$–$C_4$alkyl or by $C_1$–$C_4$alkoxy; or is phenyl, benzyl or naphthyl, or phenyl, benzyl or naphthyl each substituted by $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$alkylsulfinyl, nitro, cyano, $COOR_{27}$, $NR_{25}R_{26}$, $CONR_{28}R_{29}$ or by $SO_2NR_{30}R_{14}$; or is $C_1$–$C_6$alkyl substituted by $C_1$–$C_4$alkoxy, $C_3$–$C_6$cycloalkyl, cyano, $COOR_{24}$ or by $CONR_{32}R_{33}$; or is $C_3$–$C_6$alkenyl, $C_3$–$C_6$haloalkenyl, $C_3$–$C_6$alkynyl, $C_3$–$C_6$-haloalkynyl, $X_3R_{35}$ or $X_4R_{36}$; $R_{13}$ is hydrogen, $C_1$–$C_6$alkyl, $C_3$–$C_6$alkenyl, $C_3$–$C_6$alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ and $R_{25}$ are each independently of the other the groups —C(O)—$X_5$—$C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_5$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_4$alkyl or $C_1$–$C_4$haloalkyl; $R_{23}$ and $R_{36}$ are each independently of the other $C_1$–$C_4$alkyl substituted by $COOR_{34}$; $R_{24}$, $R_{27}$ and $R_{34}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; and $R_{37}$ is hydrogen, $C_1$–$C_4$alkyl, $C_3$–$C_6$alkenyl or $C_3$–$C_6$alkynyl; or an N-oxide or a salt of a compound of formula I, and b) a herbicide-antagonistically effective amount of a sulfamoylphenylurea of formula II

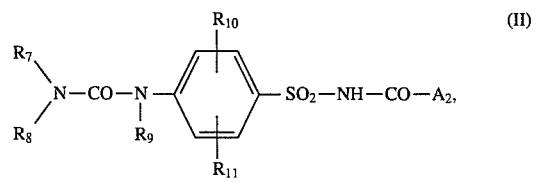

wherein $A_2$ is a radical from the group

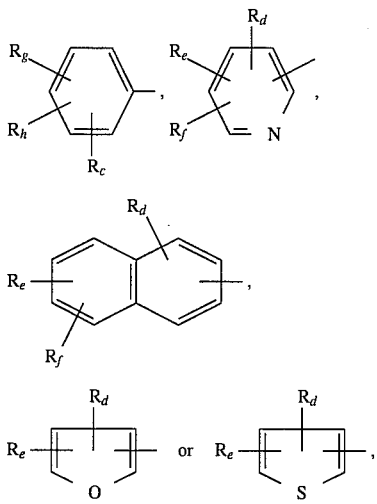

$R_7$ and $R_8$ are each independently of the other hydrogen, $C_1$–$C_8$alkyl, $C_3$–$C_8$cycloalkyl, $C_3$–$C_6$alkenyl, $C_3$–$C_6$alkynyl or

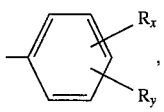

or are $C_1$–$C_4$alkyl substituted by $C_1$–$C_4$alkoxy or by

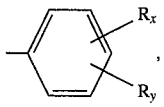

$R_7$ and $R_8$ together form a $C_4$–$C_6$alkylene bridge, or a $C_4$–$C_6$alkylene bridge interrupted by oxygen, sulfur, SO, $SO_2$, NH or by —N($C_1$–$C_4$alkyl)—; $R_9$ is hydrogen or $C_1$–$C_4$alkyl; $R_{10}$ and $R_{11}$ are each independently of the other hydrogen, halogen, cyano, nitro, trifluoromethyl, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$, $CONR_kR_m$, —$COR_n$, —$SO_2NR_kR_m$ or —$OSO_2$—$C_1$–$C_4$alkyl; or $R_{10}$ and $R_{11}$ together form a $C_3$–$C_4$alkylene bridge, which may be substituted by halogen or by $C_1$–$C_4$alkyl, or a $C_3$–$C_4$alkenylene bridge, which may be substituted by halogen or by $C_3$- or $C_4$-alkyl, or a butadienylene bridge, which may be substituted by halogen or by $C_1$–$C_4$alkyl, and $R_g$ and $R_h$ are each independently of the other hydrogen, halogen, $C_1$–$C_4$alkyl, trifluoromethyl, methoxy, methylthio or —$COOR_j$; $R_c$ is hydrogen, halogen, $C_1$–$C_4$alkyl or methoxy; $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or —$CONR_kR_m$; and $R_e$ is hydrogen, halogen, halo-$C_1$–$C_4$alkyl, $C_1$–$C_4$alkyl, —$COOR_j$, trifluoromethyl or methoxy; or $R_d$ and $R_e$ together form a $C_3$–$C_4$alkylene bridge;

$R_f$ is hydrogen, halogen or $C_1$–$C_4$alkyl;

$R_x$ and $R_y$ are each independently of the other hydrogen, halogen, $C_1$–$C_4$alkyl, $C_1$–$C_4$-alkoxy, $C_1$–$C_4$alkylthio, —$COOR_{17}$, trifluoromethyl, nitro or cyano; $R_{17}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy; or is furoyl or thienyl; or is $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl or by di-$C_1$–$C_4$alkylaminocarbonyl; or is phenylaminocarbonyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy or that is mono-substituted in the phenyl ring by cyano or by nitro; or is dioxolan-2-yl that is unsubstituted or substituted by one or two $C_1$–$C_4$alkyl radicals; or is dioxan-2-yl that is unsubstituted or substituted by one or two $C_1$–$C_4$alkyl radicals; or is $C_1$–$C_4$alkyl that is substituted by cyano, nitro, carboxy or by $C_1$–$C_8$alkylthio-$C_1$–$C_8$alkoxycarbonyl; $R_j$, $R_k$ and $R_m$ are each independently of the others hydrogen or $C_1$–$C_4$alkyl; or $R_k$ and $R_m$ together form a $C_4$–$C_6$alkylene bridge, or a $C_4$–$C_6$alkylene bridge interrupted by oxygen, NH or by —N($C_1$–$C_4$alkyl)—; and $R_n$ is $C_1$–$C_4$alkyl, phenyl, or phenyl substituted by halogen, $C_1$–$C_4$alkyl, methoxy, nitro or by trifluoromethyl; or a salt of a compound of formula II.

The present invention relates also to the use of the composition according to the invention in the control of weeds and grasses in crops of useful plants, especially maize and sugar cane.

Halogen in the definitions is to be understood as being fluorine, chlorine, bromine and iodine, but preferably fluorine, chlorine and bromine, especially chlorine. Alkyl is to be understood as being straight-chain or branched alkyl; for example methyl, ethyl, n-propyl, isopropyl or the four isomers of butyl. Longer-chained alkyl groups include the isomers of pentyl, hexyl, heptyl or octyl, the unbranched chains being preferred in each case. Alkoxy is to be understood as being: methoxy, ethoxy, n-propoxy, isopropoxy or the four isomers of the butoxy, pentyloxy and hexyloxy radicals, but especially methoxy, ethoxy or isopropoxy. Alkyl substituted by alkoxy is preferably methoxymethyl, ethoxymethyl, methoxyethyl and ethoxyethyl, but especially methoxyethyl. Alkyl that is substituted by unsubstituted or substituted phenyl is preferably a derivative of phenylethyl or benzyl. Typical alkenyl and alkynyl radicals are allyl, 2-butenyl, methallyl, 3-butenyl, propargyl, 2-butynyl, 3-butynyl or 2-pentenyl. Examples of cycloalkyl are cyclopropyl, cyclopentyl, cyclohexyl or cycloheptyl, but preferably cyclopentyl and cyclohexyl. Heterocycles are, for example, pyrrolidine, piperidine, pyrazolidine, imidazolidine, oxazolidine, thiazolidine, morpholine, thiomorpholine, piperazine or hexahydroazepine and also, in the case of sulfur-containing rings, the oxidation products thereof. $C_3$–$C_6$cycloalkyl interrupted by oxygen is, for example, oxetane, oxolane, oxane, oxepane or dioxane. In alkylthio, alkylsulfinyl or alkylsulfonyl, alkyl has the specific meanings listed above.

When substituents together form a $C_3$–$C_4$alkylene bridge, $C_3$–$C_4$alkenylene bridge or butadienylene bridge, each of which may be substituted by halogen or by $C_1$–$C_4$alkyl, there are formed, for example together with a phenyl ring to which the bridge is attached, binuclear systems, such as, for example, 1,2,3,4-tetrahydronaphthalene, 1-chloro-2-methyl-3,4-dihydronaphthalene, indane, 1,2-dihydronaphthalene, indene, naphthalene, 2-methylnaphthalene, 1-n-butylnaphthalene, 2-ethylnaphthalene or 1-chloronaphthalene.

When substituents together form a $C_3$- or $C_4$-alkylene bridge, there are formed, together with the ring system to which they are attached, polynuclear systems, such as, for example, 2,3-tetramethylenethiophene, 2,3-trimethylenethiophene, 2,3-tetramethylenefuran, 3,4-tetramethylenepyridine or

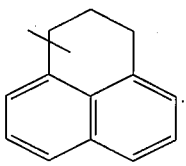

N-oxides of a compound of formula I are to be understood as being compounds that comprise a group of the formula

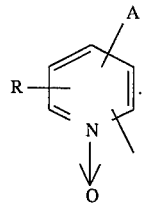

The invention relates also to the salts that can be formed by the compounds of formulae I and II with amines, alkali and alkaline earth metal bases or quaternary ammonium bases. Salt formation can also be effected by the addition of a strong acid to the pyrimidine moiety of the compound of formula I. Suitable acids for that purpose are hydrochloric acid, hydrobromic acid, sulfuric acid and nitric acid.

Of the alkali and alkaline earth metal hydroxides as salt-forming agents, special mention should be made of the hydroxides of lithium, sodium, potassium, magnesium and calcium, but especially those of sodium and potassium.

Examples of amines suitable for ammonium cation formation are both ammonia and primary, secondary and tertiary $C_1$–$C_4$alkylamines, $C_1$–$C_4$hydroxyalkylamines and $C_2$–$C_4$alkoxyalkylamines, for example methylamine, ethylamine, n-propylamine, isopropylamine, the four isomers of butylamine, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl- 2-amine, dibutenyl-2-amine, n-hexenyl-2-amine, propylenediamine, diethanoiamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, such as, for example, pyridine, quinoline, isoquinoline, morpholine, piperidine, pyrrolidine, indoline, quinuclidine and azepine; primary arylamines, such as, for example, anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

Examples of quaternary ammonium bases are generally the cations of haloammonium salts, for example the tetramethylammonium cation, the trimethylbenzylammonium cation, the triethylbenzylammonium cation, the tetraethylammonium cation, the trimethylethylammonium cation, and also the ammonium cation.

Preferably, $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen.

In formula I in preferred compositions according to the invention, $R_6$ is hydrogen, $C_1$–$C_6$alkyl or $C_3$–$C_6$cycloalkyl, especially preferably hydrogen or $C_1$–$C_6$alkyl. Also preferred are compositions according to the invention in which compounds of formula I are used wherein $R_3$ is $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_3$–$C_6$cycloalkyl, which may for its part be interrupted by oxygen; or is $C_3$–$C_6$alkenyl, or $C_3$–$C_6$alkenyl that is mono- or poly-substituted by halogen, $C_1$–$C_6$alkoxy, $C_3$–$C_6$alkenyloxy or by $C_3$–$C_6$alkynyloxy; or is $C_4$–$C_6$cycloalkyl, or $C_4$–$C_6$cycloalkyl that is mono- or poly-substituted by halogen or by $C_1$–$C_6$alkoxy or may be interrupted by oxygen; or is $C_3$–$C_6$alkynyl, and $R_6$ is hydrogen or $C_1$–$C_6$alkyl.

Compounds of formula I preferred for use in the composition according to the invention are also those wherein the pyridylsulfonylurea corresponds to the formula Ia

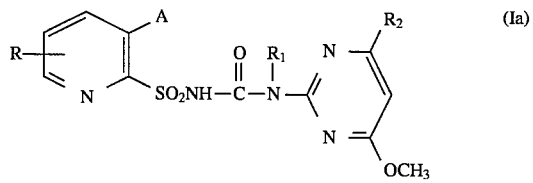

wherein A, R, $R_1$ and $R_2$ are as defined under formula I.

Compositions according to the invention that comprise that compound of formula Ia together with a compound of formula IIf

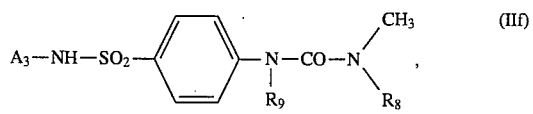

wherein $R_8$ and $R_9$ are as defined under formula H and $A_3$ is the group

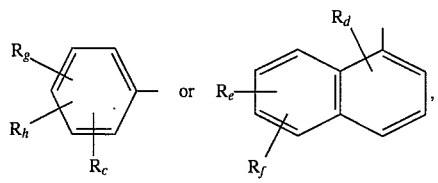

are especially preferred, $R_8$ and $R_9$ in formula IIf each being especially hydrogen or methyl.

Especially preferred among these compositions are those in which a) R is hydrogen; or b) A is —X—$R_3$; or c) A is —N—($R_4$)$R_5$; $R_5$ preferably being C(O)$R_6$.

In addition, valuable compositions according to the invention are those in which a herbicide of formula Ia is used, wherein each of R and $R_1$ is hydrogen and A is difluoromethoxy or the group

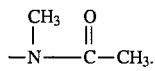

Especially outstanding compositions comprise a compound of formula Ia wherein each of R and $R_1$ is hydrogen and A is the group

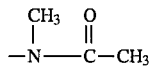

or —$SO_2$—$C_1$-$C_4$alkyl.

Compounds of formula II preferred for use in the composition according to the invention are those in which $A_2$ is a radical of the formula

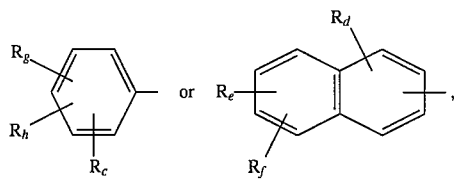

wherein $R_g$ and $R_h$ are each independently of the other hydrogen, halogen, $C_1$-$C_4$alkyl, trifluoromethyl, methoxy, methylthio or COO$R_j$; $R_c$ is hydrogen, halogen, $C_1$-$C_4$alkyl or methoxy; $R_d$ is hydrogen, halogen, nitro, $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, —COO$R_j$ or —CON$R_k R_m$; and $R_e$ is hydrogen, halogen, $C_1$-$C_4$alkyl, —COO$R_j$, trifluoromethyl or methoxy; or $R_d$ and $R_e$ together form a $C_3$- or $C_4$-alkylene bridge; $R_f$ is hydrogen, halogen or $C_1$-$C_4$alkyl; $R_j$, $R_k$ and $R_m$ are each independently of the others hydrogen or $C_1$-$C_4$alkyl; or $R_k$ and $R_m$ together form a $C_4$-$C_6$alkylene bridge, or a $C_4$-$C_6$alkylene bridge interrupted by oxygen, NH or by —N($C_1$-$C_4$alkyl)—.

Of the above compounds of formula II, those wherein $R_c$, $R_d$, $R_e$, $R_g$ and $R_h$ are each independently of the others hydrogen, $C_1$-$C_4$alkyl or methoxy are especially preferred.

Further especially suitable groups of compounds of formula II are those wherein each of $R_{10}$ and $R_{11}$ or each of $R_8$ and $R_9$ is hydrogen.

Special mention should also be made of those compounds of formula II wherein each of $R_9$, $R_{10}$ and $R_{11}$ is hydrogen.

Especially valuable compositions according to the present invention are those which comprise, as compound of formula I, a compound of formula Ia

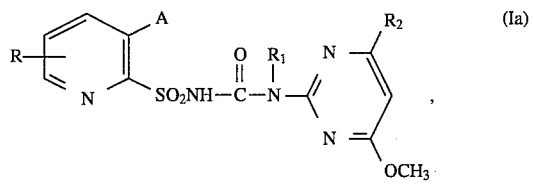

wherein A, R, $R_1$, $R_2$ and $R_3$ are as defined under formula I; and, as compound of formula II, a compound of formula IIa

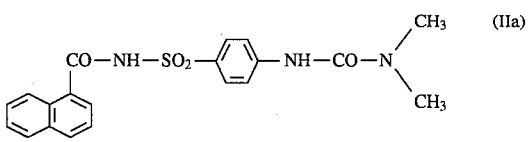

or of formula IIb

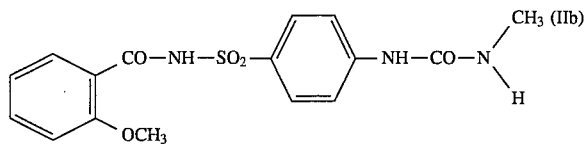

or of formula IIc

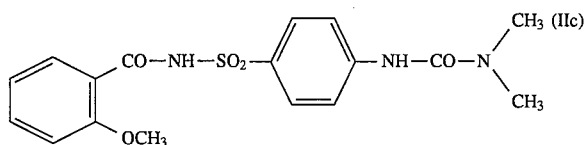

or of formula IId

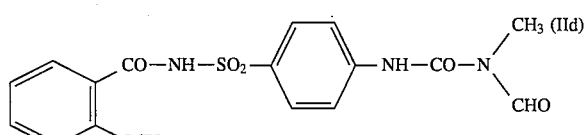

or of formula IIe

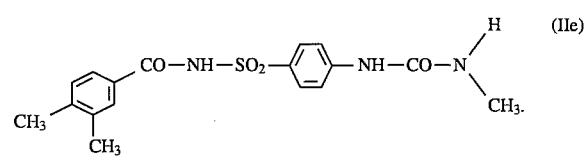

The pyridylsulfonylureas of formula I used according to the invention either are known or can be prepared analogously to known methods. The preparation of such compounds is described, for example, in EP-A-0 103 543, EP-A-0 459 949, EP-A-0 555 770 and WO 92/16522. The sulfamoylphenylureas of formula II used for the compositions according to the invention and the preparation of those ureas are known, for example, from EP-A-0 365 484.

Other herbicidally active pyridylsulfonylureas especially suitable for use in the composition according to the invention correspond to formula Ib

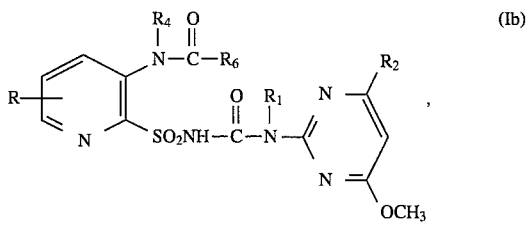

wherein R, $R_1$, $R_2$, $R_4$ and $R_6$ are as defined under formula I. Of these compounds of formula Ib, those in which $R_6$ is hydrogen or $C_1$-$C_6$alkyl are preferred.

Also preferred are those compounds of formula Ib in which each of R and $R_1$ is hydrogen. Of particular value in that group are compounds in which each of $R_4$ and $R_6$ is methyl.

The compounds of formula Ib can be prepared as follows:

a) a pyridylsulfonamide of formula III

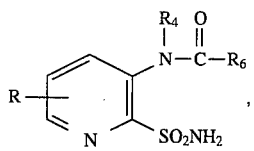   (III)

wherein R, $R_4$ and $R_6$ are as defined under formula I, is reacted in the presence of a base with a N-pyrimidinyl carbamate of formula IV

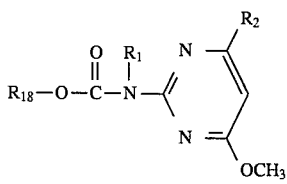   (IV)

wherein $R_1$ and $R_2$ are as defined under formula I and $R_{18}$ is $C_1$–$C_4$alkyl, or is phenyl which may be substituted by $C_1$–$C_4$alkyl or by halogen; or b) a 2-pyridylsulfonyl chloride of formula VII

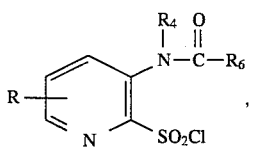   (VII)

wherein R, $R_4$ and $R_6$ are as defined under formula I, is reacted in the presence of a base and in an inert, organic solvent with a metal cyanate of formula VIII

   (VIII), wherein M⊕ is an ammonium, phosphonium, sulfonium or an alkali metal cation, and with a 2-aminopyrimidine of formula IX

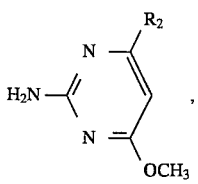   (IX)

wherein $R_1$ and $R_2$ are as defined under formula I, or c) a pyridylsulfonamide of formula III

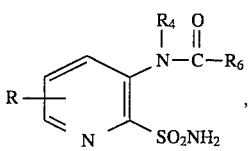   (III)

wherein R, $R_4$ and $R_6$ are as defined under formula I, is reacted in the presence of a base with a 2-pyrimidinyl isocyanate of formula X

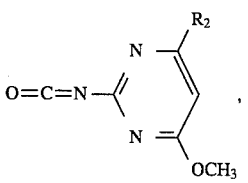   (X)

wherein $R_2$ is as defined under formula I.

The reactions to form compounds of formula Ib are advantageously carried out in aprotic, inert organic solvents.

Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide, diethylformamide or N-methylpyrrolidinone. The reaction temperatures are preferably from −20° to +120° C.

The reactions are generally slightly exothermic and can be carried out at room temperature. It is expedient to heat the reaction mixture briefly to boiling point in order to reduce the reaction time or also to initiate the reaction. The reaction times can also be reduced by adding a few drops of base as a reaction catalyst. Suitable bases are especially tertiary amines, such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. The bases used may, however, also be inorganic bases, such as hydrides, such as sodium or calcium hydride, hydroxides, such as sodium and potassium hydroxide, carbonates, such as sodium and potassium carbonate, or hydrogen carbonates, such as potassium and sodium hydrogen carbonate.

The end products of formula Ib can be isolated by concentration and/or evaporation of the solvent and purified by recrystallisation or trituration of the solid residue in solvents in which they are not readily soluble, such as ethers, aromatic hydrocarbons or chlorinated hydrocarbons.

The 2-pyrimidinyl isocyanates of formula X can be prepared from the corresponding 2-aminopyrimidines by known methods. Such methods are described, for example, in U.S. Pat. No. 3,919,228 and in U.S. Pat. No. 3,732,223.

The intermediates of formula IV can be prepared analogously to known processes. The compounds of formula III are known or can be prepared by known methods. Compounds of formula III are known, for example, from EP-A-0 555 770 and can also be prepared analogously to the processes described in EP-A-0 314 505 and EP-A-0 459 949. Processes for the preparation of N-pyrimidinyl carbamates are described, for example, in EP-A-0 101 670.

Compounds of formula III can be prepared, for example, by reacting a compound of formula V

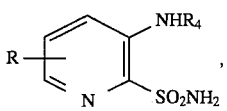   (V)

wherein R and $R_4$ are as defined under formula I, in the presence of a base, with an acylating agent of formula VI

   (VI), wherein $R_5$ is the group C(O)—$R_6$, $R_6$ is as defined under formula I and Z is a leaving group, such as, for example, halogen, $R_5$O—, $R_6$C(O)O— or imidazole. Such reactions are described, for example, in Farmaco Ed. scient. 12, 392 (1957). The compounds of formula V either are known or can be prepared by known methods which are disclosed, for example, in EP-A-0 459 949.

Pyridylsulfonamides of formula III can also be prepared from the corresponding 2-pyridylsulfonyl chlorides of formula VII by reaction with ammonia.

2-pyridylsulfonyl chlorides of formula VII can be prepared very especially advantageously by reacting a compound of formula XI

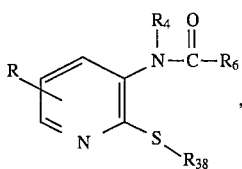

wherein R, $R_4$ and $R_6$ are as defined under formula I and $R_{38}$ is benzyl, methoxymethyl or isopropyl, with aqueous chlorine.

The compounds of formula XI are novel and the present invention relates also to those compounds. The intermediates of formula XI developed specifically for the present invention permit an economically especially advantageous preparation of the compounds of formulae VII and III, which are required for the preparation of the herbicide of formula Ib which preferred compositions according to the invention comprise.

The compounds of formula XI are prepared by reacting a compound of formula XII

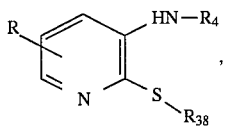

wherein R, $R_4$ and $R_{38}$ are as defined above, in the presence of a base, with a compound of formula VI $$Z—R_5 \qquad (VI),$$

wherein $R_5$ is the group C(O)—$R_6$, $R_6$ is as defined under formula I and Z is a leaving group, such as, for example, halogen, $R_5O—$, $R_6C(O)O—$ or imidazole.

Compounds of formula XII can be prepared by reacting, for example, a compound of formula XIV

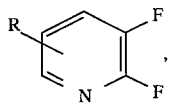

wherein R is as defined under formula I, with benzyl mercaptan or isopropyl mercaptan in the presence of a base to form a compound of formula XIII

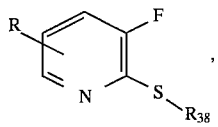

wherein $R_{38}$ is benzyl, methoxymethyl or isopropyl and R is as deemed under formula I, and converting the latter in the presence of a base into a compound of formula XII by reaction with a compound of formula XV $$H_2NR_4 \qquad (XV),$$

wherein $R_4$ is as defined under formula I.

The invention relates also to a method of selectively controlling weeds in crops of useful plants, which comprises treating the useful plants or the crop area thereof with a herbicidally effective amount of a pyridylsulfonylurea of formula I and a herbicide-antagonistically effective amount of a sulfamoylphenylurea of formula II, simultaneously or independently of one another.

Cultivated plants that can be protected against the harmful effect of the above-mentioned herbicides of formula I are especially those that are of importance in the fields of food and textiles, for example sugar cane and, especially, sorghum and maize, and also rice and other species of cereal, such as wheat, rye, barley and oats. The composition according to the invention is especially suitable for protecting maize crops and sugar cane crops against the herbicidal action of the compounds of formula I.

The weeds to be controlled may be both monocots and dicots.

There come into consideration as cultivated plants or parts of those plants, for example, those mentioned above. Crop areas are areas of land on which the cultivated plants are already growing or in which the seeds of those cultivated plants have been sown, and also areas of land on which it is intended to grow those cultivated plants.

A safener of formula II may, depending on the purpose, be used to pre-treat the seed material of the cultivated plant (dressing the seed or the seedlings) or may be incorporated into the soil before or after sowing. It may, however, also be applied, alone or together with the herbicide, after the emergence of the plants. The treatment of the plants or seed with the safener can therefore, in principle, be effected independently of the time at which the herbicide is applied. The treatment of the plant can, however, also be carried out by applying the herbicide and the safener simultaneously (for example in the form of a tank mixture).

The rate of application of the safener in relation to the herbicide depends largely on the method of application. In the case of field treatment, which is effected either using a tank mixture with a combination of the safener and the herbicide or by the separate application of the safener and the herbicide, the ratio of safener to herbicide is generally from 1:100 to 1:1, preferably from 1:20 to 1:1, and especially 1:1. In contrast, in the case of seed dressing, much smaller amounts of safener are required in relation to the rate of application of herbicide per hectare of crop area.

In the case of field treatment, from 0.001 to 5.0 kg safener/ha, preferably from 0.005 to 0.5 kg safener/ha, are generally applied.

The rate of application of herbicide is generally from 0.001 to 2 kg/ha, but preferably from 0.001 to 0.5 kg/ha.

In the case of seed dressing, from 0.001 to 10 g safener/kg seed, preferably from 0.05 to 2 g safener/kg seed are generally applied. If the safener is applied in liquid form by seed soaking shortly before sowing, then it is advantageous to use safener solutions that comprise the active ingredient in a concentration of from 1 to 10 000, preferably from 100 to 1000 ppm.

For the purpose of application, the compounds of formula II or combinations of compounds of formula II and the herbicides to be antagonism are advantageously used together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions to be used, the methods of application, such as spraying, atomising, dusting, scattering, coating or pouring, are chosen in accordance with the intended objectives and the prevailing circumstances.

The formulations, i.e. the compositions, preparations or mixtures comprising the compound (active ingredient) of formula II or a combination of the compound of formula II and the herbicide of formula I to be antagonised and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalic acid esters, such as dibutyl or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, and also vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula II to be formulated, and, where appropriate, also the herbicide of formula I to be antagonised, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"Mc Cutcheon's Detergents and Emulsifiers Annual" MC Publishing Corp., Ridgewood, N.J., 1981. Stache, H., "Tensid-Taschenbuch", Carl Hanser Verlag, Munich/Vienna, 1981.

The agrochemical compositions generally comprise 0.1 to 99% by weight, preferably 0.1 to 95% by weight, of a compound of formula II or a mixture of antidote and herbicide, 1 to 99.9% by weight, preferably 5 to 99.8% by weight, of a solid or liquid adjuvant and 0 to 25% by weight, preferably 0.1 to 25% by weight, of a surfactant.

Whereas commercial products will preferably be formulated as concentrates, the end user will normally employ dilute formulations.

The compositions may also comprise further ingredients such as stabilisers, antifoams, viscosity regulators, binders and tackifiers, as well as fertilisers or other active ingredients for obtaining special effects.

There are various suitable methods and techniques for using the compounds of formula II or the compositions comprising them for protecting cultivated plants against the harmful effects of herbicides of formula I; the following are examples:

i) Seed dressing a) Dressing the seeds with a wettable powder formulation of a compound of formula II by shaking in a vessel until the formulation is uniformly distributed over the seed surface (dry dressing). Approximately from 1 to 500 g of compound of formula II (from 4 g to 2 kg of wettable powder) are used per 100 kg of seed.

b) Dressing the seeds with an emulsifiable concentrate of a compound of formula II according to method a) (wet dressing).

c) Dressing by immersing the seed in a mixture comprising from 100 to 1000 ppm of compound of formula II for from 1 to 72 hours and, if desired, subsequently drying the seeds (immersion dressing).

Dressing the seed or treating the germinated seedlings are naturally the preferred methods of application because the treatment with the active ingredient is directed wholly at the target crop. Generally from 1 to 1000 g of antidote, preferably from 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application from a tank mixture

A liquid formulation of a mixture of antidote and herbicide (ratio of the one to the other from 10:1 to 1:100) is used, the rate of application of herbicide being from 0.01 to 5.0 kg per hectare. Such a tank mixture is applied before or after sowing.

iii) Application to the seed furrow

The antidote is introduced into the open, sown seed furrow in the form of an emulsifiable concentrate, a wettable powder or granules and, after the seed furrow has been covered, the herbicide is applied preemergence in the normal manner.

iv) Controlled release of the active ingredient

The compound of formula II is applied in solution to mineral granulated carriers or polymerised granules (urea/formaldehyde) and dried. If desired, a coating may be applied (coated granules) which enables the active ingredient to be released in metered amounts over a predetermined period of time.

The compounds of formulae I and II may be formulated either separately or together. Preferred formulations have especially the following composition (throughout, percentages are by weight):

| Emulsifiable concentrates: | |
| --- | --- |
| active ingredient: | 1 to 20%, preferably 5 to 10% |
| surface-active agent: | 5 to 30%, preferably 10 to 20% |
| liquid carrier: | 15 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

Preparation Examples

Example P1: Preparation of 3-(N-methyl-N-methylcarbonylamino)-pyridin-2-yl-sulfonamide

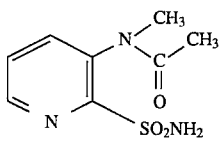

0.89 ml of pyridine and 0.82 ml of acetyl bromide are added in succession at room temperature to a solution of 1.87 g of 3-N-methylaminopyridin-2-yl-sulfonamide in 40 ml of dry acetonitrile. After 30 minutes a further 0.3 ml of acetyl bromide is added. After stirring for 60 minutes, 0.32 ml of pyridine is added. After stirring for 30 minutes, the reaction mixture is filtered to give 0.8 g of 3-(N-methyl-N-methylcarbonylamino)pyridin- 2-yl-sulfonamide which has a melting point of from 181° to 185° C.

Example P2: Preparation of N-(N-methyl-N-methylcarbonylamino)-pyridin-2-yl-sulfonyl-N'-(4-methoxy-6-methylpyrimidin-2-yl)urea (Compound No. 1.02)

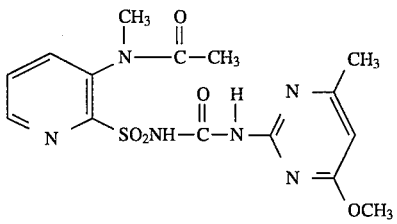
(1.01)

2.18 ml of 1,5-diazabicyclo[5.4.0]undec-5-ene and 3.89 g of N-(4-methoxy-6-methyl-pyrimidin-2-yl)-phenyl carbamate are added in succession to a solution of 3.07 g of 3-(N-methyl-N-methylcarbonylamino)-pyridin- 2-yl-sulfonamide in 50 ml of acetonitrile. After stirring for 45 minutes, the reaction mixture is concentrated in vacuo, the oily residue is triturated with 10 ml of 2N hydrochloric acid and then diluted with 10 ml of water. The crystalline product is filtered and then washed with water and diethyl ether to give 5.25 g of N-(N-methyl-N-methylcarbonylamino)-pyridin-2-yl-sulfonyl-N'-(4-methoxy-6-methylpyrimidin- 2-yl)urea (Compound No. 1.01 ) which has a melting point of from 182° to 184° C.

Example P3: Preparation of 3-(N-methyl-N-methylcarbonylamino)-pyridin-2-yl-sulfonyl chloride

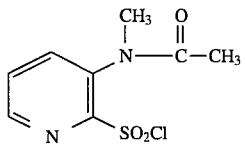

4.6 g of chlorine gas are introduced over a period of 15 minutes at a temperature of −5° C. into an emulsion of 3.6 g of 3-(N-methyl-N-methylcarbonylamino)-2-isopropylthiopyridine in 35 ml of methylene chloride and 48 ml of 1N hydrochloric acid and the batch is stirred for a further 15 minutes. Nitrogen is then passed through the reaction mixture over a period of 20 minutes at the same temperature. After separating the phases and washing three times with methylene chloride and ice-water, the reaction mixture is dried with sodium sulfate and filtered. The resulting solution of N-(N-methyl-N-methyl-carbonylamino)-pyridin- 2-yl-sulfonyl chloride (60 ml) can be reacted directly either to form the corresponding sulfonamide (Example P1) or to form the sulfonylureas of formula I wherein R is hydrogen and each of $R_4$ and $R_6$ is methyl.

Example P4: Preparation of 3-(N-methyl-N-methylcarbonylamino)-2-isopropylthiopyridine

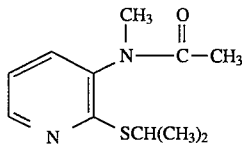

1.34 ml of acetyl bromide are added dropwise at a temperature of from 0° to 2° C. to a solution of 2.73 g of 3-N-methyl-2-isopropylthiopyridine in 40 ml of acetonitrile. The reaction mixture is then stirred for 20 minutes at 0° C. After adding 1.33 ml of pyridine and stirring for one hour, the reaction mixture is concentrated and ethyl acetate/water is added.

After washing 3 times with ethyl acetate and once with water, the reaction mixture is dried over sodium sulfate and then concentrated by evaporation to give 3.25 g of N-(N-methyl-N-methylcarbonylamino)- 2-isopropylthiopyridine which, after recrystallisation from petroleum ether, has a melting point of from 49° to 51 ° C.

Example P5: Preparation of 3-N-methylamino-2-isopropylthiopyridine

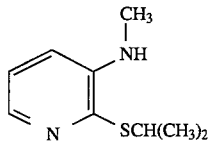

45 g of methylamine gas are added under pressure to 8.56 g of 3-fluoro-2-isopropylthiopyridine in a pressure vessel and the reaction mixture is maintained at a temperature of 140° C. for 24 hours and then at 150° C. for 16 hours. After filtering and concentrating the reaction mixture by evaporation, purification is effected by column chromatography (ethyl acetate/hexane 1:9) to give 6.77 g of 3-N-methylamino-2-isopropylthiopyridine which has a melting point of from 37° to 38° C.

Example P6: Preparation of 3-fluoro-2-isopropylthiopyridine

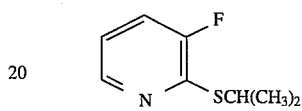

220.93 g of isopropyl mercaptan are added dropwise at a temperature of from 0° to –5° C. to a mixture of 388.6 g of potassium carbonate and 301 g of 2,3-difluoropyridine in 4300 ml of dimethylformamide. After stirring for 20 minutes, the temperature of the reaction mixture is allowed to rise slowly to room temperature and is stirred for a further 30 minutes. The reaction mixture is then added to an ice-water/ethyl acetate mixture, the phases are washed four times with ethyl acetate and ice-water and then dried over sodium sulfate. After filtering and concentrating by evaporation, the resulting crude product (510 g) is purified by column chromatography (ethyl acetate/hexane 1:9) to give 327.3 g of 3-fluoro-2-isopropylthiopyridine in the form of an oil.

The compounds of formulae I, Ib and III listed in the following Tables are prepared in an analogous manner.

TABLE 1

Compounds of formula Ib

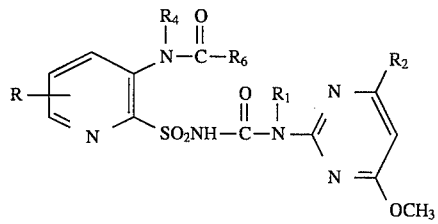

(Ib)

| Comp. No. | R | $R_4$ | $R_6$ | $R_1$ | $R_2$ | m.p. [°C.] |
|---|---|---|---|---|---|---|
| 1.01 | H | $CH_3$ | $CH_3$ | H | $OCH_3$ | 178–180 |
| 1.02 | H | $CH_3$ | $CH_3$ | H | $CH_3$ | 182–184 |
| 1.03 | H | H | $CH_3$ | H | $OCH_3$ | 162–164 |
| 1.04 | H | H | $CH_3$ | H | $OCH_3$ | 151–152 |
| 1.05 | 6-$CH_3$ | $CH_3$ | $CH_3$ | H | $OCH_3$ | |
| 1.06 | 6-$CH_3$ | $CH_3$ | $CH_3$ | H | $CH_3$ | |

TABLE 1-continued

Compounds of formula Ib

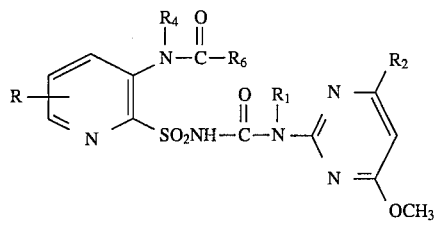

| Comp. No. | R | $R_4$ | $R_6$ | $R_1$ | $R_2$ | m.p. [°C.] |
|---|---|---|---|---|---|---|
| 1.07 | H | $C_2H_5$ | $CH_3$ | H | $OCH_3$ | |
| 1.08 | H | $C_3H_7$-(i) | $CH_3$ | H | $OCH_3$ | |
| 1.09 | H | H | $CHCl_2$ | H | $OCH_3$ | |
| 1.10 | H | H | $CHCl_2$ | H | $CH_3$ | |
| 1.11 | 6-$CH_3$ | $CH_3$ | $CHCl_2$ | H | $OCH_3$ | |
| 1.12 | H | H | $CHCl_2$ | H | $CH_3$ | |
| 1.13 | H | H | $CH_2Cl$ | H | $CH_3$ | |
| 1.14 | H | H | $CH_2Cl$ | H | $OCH_3$ | |
| 1.15 | H | H | $CF_3$ | H | $OCH_3$ | |
| 1.16 | H | H | $CF_3$ | H | $CH_3$ | |
| 1.17 | H | $CH_3$ | $CF_3$ | H | $CH_3$ | |
| 1.18 | H | $CH_3$ | $CF_3$ | H | $OCH_3$ | |
| 1.19 | 6-$CH_3$ | $CH_3$ | $CF_3$ | H | $OCH_3$ | |
| 1.20 | 6-$CH_3$ | H | H | H | $OCH_3$ | |
| 1.21 | 6-$CH_3$ | $CH_3$ | H | H | $OCH_3$ | |
| 1.22 | H | H | H | H | $OCH_3$ | |
| 1.23 | H | H | H | H | $CH_3$ | |
| 1.24 | H | H | $-CH_2=CH_2$ | H | $CH_3$ | |
| 1.25 | H | $CH_3$ | $-CH_2=CH_2$ | H | $OCH_3$ | 163–165 |
| 1.26 | H | H | $-CH\equiv CH$ | H | $CH_3$ | |
| 1.27 | H | H | $-CH\equiv CH$ | H | $OCH_3$ | |
| 1.28 | H | H | cyclopropyl | H | $OCH_3$ | |
| 1.29 | H | H | cyclopropyl | H | $CH_3$ | |
| 1.30 | H | H | cyclopropyl | H | $CH_3$ | |
| 1.31 | H | $CH_3$ | cyclopropyl | H | $OCH_3$ | |
| 1.32 | 6-$CH_3$ | $CH_3$ | cyclopropyl | H | $OCH_3$ | |
| 1.33 | H | H | phenyl | H | $OCH_3$ | 150–152 |
| 1.34 | H | $CH_3$ | phenyl | H | $OCH_3$ | |
| 1.35 | H | $CH_3$ | phenyl | H | $CH_3$ | |

TABLE 1-continued

Compounds of formula Ib (Ib)

| Comp. No. | R | R₄ | R₆ | R₁ | R₂ | m.p. [°C.] |
|---|---|---|---|---|---|---|
| 1.36 | H | CH₃ | 2-Cl-phenyl | H | OCH₃ | |
| 1.37 | H | H | 2-Cl-phenyl | H | OCH₃ | 181–183 |
| 1.38 | 6-CH₃ | H | 2-Cl-phenyl | H | OCH₃ | |
| 1.39 | 6-CH₃ | CH₃ | 2-Cl-phenyl | H | OCH₃ | |
| 1.40 | H | CH₃ | 3-Cl-phenyl | H | OCH₃ | 187–189 |
| 1.41 | H | CH₃ | 4-Cl-phenyl | H | OCH₃ | 168–170 |
| 1.42 | 6-CH₃ | CH₃ | 4-Cl-phenyl | H | OCH₃ | |
| 1.43 | H | CH₃ | 4-Cl-phenyl | H | CH₃ | |
| 1.44 | H | H | 4-Cl-phenyl | H | OCH₃ | |
| 1.45 | H | CH₃ | 3,4-di-Cl-phenyl | H | OCH₃ | 179–182 |

TABLE 1-continued
Compounds of formula Ib
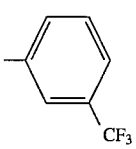
(Ib)
| Comp. No. | R | R₄ | R₆ | R₁ | R₂ | m.p. [°C.] |
|---|---|---|---|---|---|---|
| 1.46 | H | CH₃ | 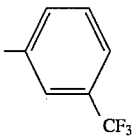 | H | OCH₃ | |
| 1.47 | H | H | 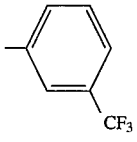 | H | OCH₃ | |
| 1.48 | H | CH₃ | 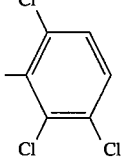 | H | CH₃ | |
| 1.49 | H | CH₃ | 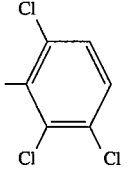 | H | OCH₃ | |
| 1.50 | H | CH₃ | 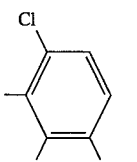 | H | CH₃ | |
| 1.51 | H | H | 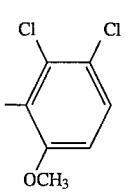 | H | CH₃ | |
| 1.52 | H | H | (2,6-Cl₂-4-OCH₃-phenyl) | H | CH₃ | |

TABLE 1-continued

Compounds of formula Ib (Ib) [structure diagram with substituents R, R₄, R₆, R₁, R₂]

| Comp. No. | R | R₄ | R₆ | R₁ | R₂ | m.p. [°C.] |
|---|---|---|---|---|---|---|
| 1.53 | H | H | 2,4-dichloro-3-methoxyphenyl | H | CH₃ | |
| 1.54 | H | H | 2,4-dichloro-3-methoxyphenyl | H | OCH₃ | |
| 1.55 | H | CH₃ | 2,4-dichloro-3-methoxyphenyl | H | OCH₃ | |
| 1.56 | H | CH₃ | 2,4-dichloro-3-methoxyphenyl | H | CH₃ | |
| 1.57 | H | CH₃ | —CH₂-(2,3,6-trichlorophenyl) | H | CH₃ | |
| 1.58 | H | CH₃ | —CH₂-(2,3,4-trichlorophenyl) | H | OCH₃ | |
| 1.59 | H | CH₃ | OCH₃ | H | OCH₃ | |
| 1.60 | H | CH₃ | OC₂H₅ | H | OCH₃ | 160–163 |
| 1.61 | H | CH₃ | OC₂H₅ | H | CH₃ | |
| 1.62 | H | H | OC₂H₅ | H | OCH₃ | |
| 1.63 | H | CH₃ | —CH₂Cl | H | OCH₃ | 182–184 |
| 1.64 | H | CH₃ | —CH₂Cl | H | CH₃ | |
| 1.65 | H | CH₃ | —CHCl₂ | H | CH₃ | |
| 1.66 | H | CH₃ | —CHCl₂ | H | OCH₃ | 180–182 |

TABLE 1-continued
Compounds of formula Ib
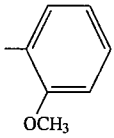
| Comp. No. | R | R₄ | R₆ | R₁ | R₂ | m.p. [°C.] |
|---|---|---|---|---|---|---|
| 1.67 | H | CH₃ | 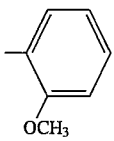 | H | OCH₃ | 142–144 |
| 1.68 | H | H | 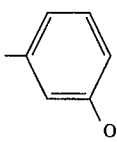 | H | OCH₃ | |
| 1.69 | H | CH₃ | 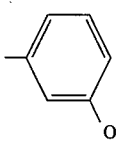 | H | OCH₃ | 177–179 |
| 1.70 | H | CH₃ | 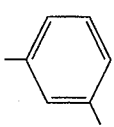 | H | CH₃ | |
| 1.71 | H | H | 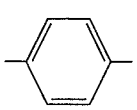 | H | OCH₃ | |
| 1.72 | H | H | 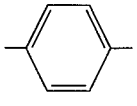 | H | OCH₃ | |
| 1.73 | H | CH₃ | 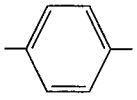 | H | OCH₃ | 188–190 |
| 1.74 | H | CH₃ | 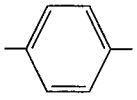 | H | CH₃ | |
| 1.75 | H | CH₃ | 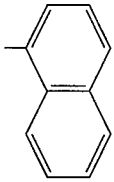 | H | OCH₃ | |

TABLE 1-continued

Compounds of formula Ib (Ib) structure with R, R4, R6, R1, R2 substituents on pyridine-sulfonylurea-pyrimidine scaffold with OCH3

| Comp. No. | R | R4 | R6 | R1 | R2 | m.p. [°C.] |
|---|---|---|---|---|---|---|
| 1.76 | H | H | 1-naphthyl | H | OCH3 | |
| 1.77 | H | CH3 | -CH2-(2,3,6-trichlorophenyl) | H | OCH3 | |
| 1.78 | H | CH3 | CH3—CCl2— | H | OCH3 | |
| 1.79 | H | CH3 | 4-Cl-C6H4-OCH2— | H | OCH3 | |
| 1.80 | H | CH3 | 4-Cl-C6H4-OCH2— | H | CH3 | 195–198 |
| 1.81 | H | CH3 | 2,4-diCl-C6H3-OCH2— | H | CH3 | |
| 1.82 | H | CH3 | 2,4-diCl-C6H3-OCH2— | H | OCH3 | 192–195 |
| 1.83 | H | CH3 | 4-Cl-2-CH3-C6H3-OCH2— | H | OCH3 | 190–193 |
| 1.84 | H | CH3 | 2-CH3-C6H4-OCH(CH3)— | H | OCH3 | |

TABLE 1-continued
Compounds of formula Ib
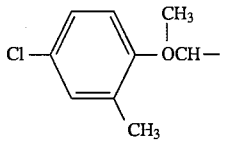
(Ib)
| Comp. No. | R | R4 | R6 | R1 | R2 | m.p. [°C.] |
|---|---|---|---|---|---|---|
| 1.85 | H | CH3 | 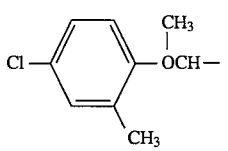 | H | OCH3 | |
| 1.86 | H | H | 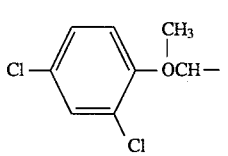 | H | OCH3 | |
| 1.87 | H | CH3 | 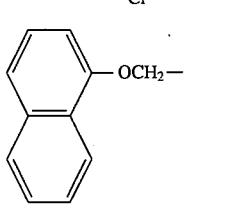 | H | OCH3 | |
| 1.88 | H | CH3 | 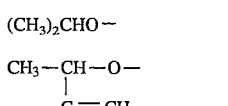 | H | OCH3 | 180–182 |
| 1.89 | H | CH3 | (CH3)2CHO— | H | OCH3 | |
| 1.90 | H | CH3 | CH3—CH—O—<br>        \|<br>       C≡CH | H | OCH3 | |
| 1.91 | H | CH3 | 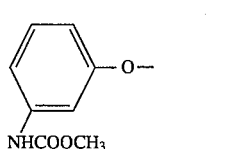 | H | OCH3 | |
| 1.92 | H | H | 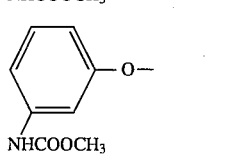 | H | OCH3 | |
| 1.93 | H | H | 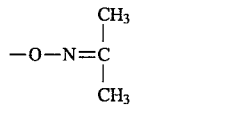 | H | OCH3 | |
| 1.94 | H | CH3 | 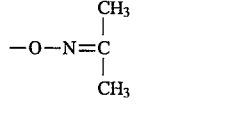 | H | OCH3 | |

TABLE 1-continued

Compounds of formula Ib

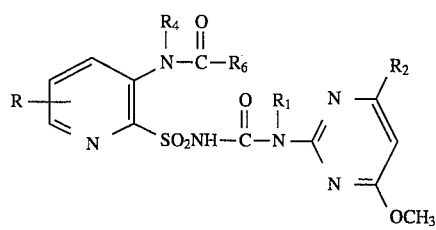

(Ib)

| Comp. No. | R | $R_4$ | $R_6$ | $R_1$ | $R_2$ | m.p. [°C.] |
|---|---|---|---|---|---|---|
| 1.95 | H | $CH_3$ | ![C(CH3)3, C(CH3)2 phenyl -O-] | H | $OCH_3$ | |
| 1.96 | H | $CH_3$ | ![3,4-dichlorobenzyl -CH2O-] | H | $OCH_3$ | |
| 1.97 | H | $CH_3$ | $C_2H_5$ | H | $OCH_3$ | 171–173 |
| 1.98 | H | $CH_3$ | $CH_2OCH_3$ | H | $OCH_3$ | 180–182 |
| 1.99 | H | $CH_3$ | H | H | $OCH_3$ | 175–177 |
| 1.100 | H | $CH_3$ | H | H | $CH_3$ | 163–165 |
| 1.101 | H | $C_2H_5$ | H | H | $OCH_3$ | 176–177 |
| 1.102 | H | $C_2H_5$ | H | H | $OCH_3$ | 192–155 |

TABLE 2

Compounds of formula III:

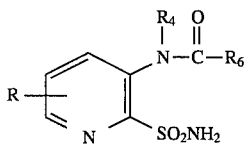

(III)

| Comp. No. | R | $R_4$ | $R_6$ | m.p. [°C.] |
|---|---|---|---|---|
| 2.01 | H | H | $CH_3$ | 172–174 |
| 2.02 | H | $CH_3$ | $CH_3$ | 181–185 |
| 2.03 | 6-$CH_3$ | $CH_3$ | $CH_3$ | |
| 2.04 | H | H | $CHCl_2$ | 190–192 |
| 2.05 | 6-$CH_3$ | $CH_3$ | $CHCl_2$ | |
| 2.06 | H | $CH_3$ | $CH_2Cl$ | |
| 2.07 | H | H | $CF_3$ | |
| 2.08 | H | $CH_3$ | $CF_3$ | |
| 2.09 | 6-$CH_3$ | $CH_3$ | $CF_3$ | |
| 2.10 | 6-$CH_3$ | H | H | |
| 2.11 | 6-$CH_3$ | $CH_3$ | H | |
| 2.12 | H | $CH_3$ | H | 120–122 |
| 2.13 | H | $CH_3$ | $-CH_2=CH_2$ | 164–166 |
| 2.14 | H | $CH_3$ | $-CH\equiv CH$ | |
| 2.15 | H | H | ▷ | |

TABLE 2-continued
Compounds of formula III:
(III)
| Comp. No. | R | R₄ | R₆ | m.p. [°C.] |
|---|---|---|---|---|
| 2.16 | H | CH₃ | 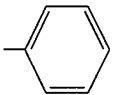 | 191–193 |
| 2.17 | H | H | 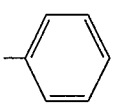 | |
| 2.18 | H | CH₃ | 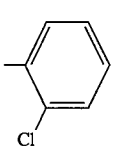 | 149–151 |
| 2.19 | H | CH₃ | 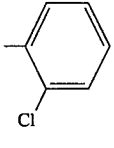 | 187–189 |
| 2.20 | H | H | 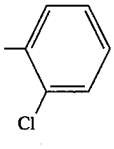 | |
| 2.21 | 6-CH₃ | H | 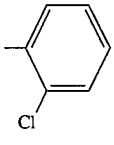 | |
| 2.22 | 6-CH₃ | CH₃ | 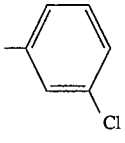 | |
| 2.23 | H | CH₃ | 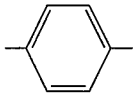 | 169–170 |
| 2.24 | H | CH₃ | 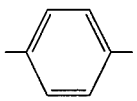 | 183–185 |
| 2.25 | 6-CH₃ | CH₃ | 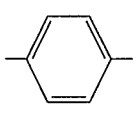 | |
| 2.26 | H | H | | |

TABLE 2-continued

Compounds of formula III:

(III)

[Structure: pyridine ring with R substituent, N(R₄)−C(=O)−R₆ group, and SO₂NH₂ group]

| Comp. No. | R | R₄ | R₆ | m.p. [°C.] |
|---|---|---|---|---|
| 2.27 | H | CH₃ | 2,5-dichlorophenyl | 179–182 |
| 2.28 | H | CH₃ | 3-(trifluoromethyl)phenyl | 161–163 |
| 2.29 | H | CH₃ | 2,3,4-trichlorophenyl | |
| 2.30 | H | H | 2,3,4-trichlorophenyl | |
| 2.31 | H | H | 2,3-dichloro-5-methoxyphenyl | |
| 2.32 | H | H | 2,5-dichloro-3-methoxyphenyl | |
| 2.33 | H | CH₃ | 2,5-dichloro-3-methoxyphenyl | |

TABLE 2-continued
Compounds of formula III:
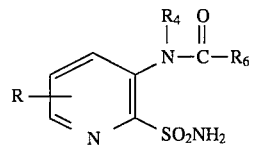
(III)
| Comp. No. | R | $R_4$ | $R_6$ | m.p. [°C.] |
|---|---|---|---|---|
| 2.34 | H | $CH_3$ | -CH$_2$-(2,6-dichloro-3-chlorophenyl) | |
| 2.35 | H | $CH_3$ | $-OCH_3$ | |
| 2.36 | H | $CH_3$ | $-OC_2H_5$ | 126–128 |
| 2.37 | H | H | $-OC_2H_5$ | |
| 2.38 | H | $CH_3$ | $-CH_2CH_3$ | 178–180 |
| 2.39 | H | $CH_3$ | 2-methoxyphenyl | 171–173 |
| 2.40 | H | H | 2-methoxyphenyl | |
| 2.41 | H | $CH_3$ | 3-methoxyphenyl | 152–154 |
| 2.42 | H | H | 3-methoxyphenyl | |
| 2.43 | H | H | 4-methoxyphenyl | 190–192 |
| 2.44 | H | $CH_3$ | 4-methoxyphenyl | |
| 2.45 | H | $CH_3$ | 1-naphthyl | 235–237 |

TABLE 2-continued

Compounds of formula III:

$$\text{(III)}$$

Structure: pyridine ring with R substituent, N(R_4)-C(=O)-R_6 group, and SO_2NH_2 group.

| Comp. No. | R | R_4 | R_6 | m.p. [°C.] |
|---|---|---|---|---|
| 2.46 | H | H | 1-naphthyl | |
| 2.47 | H | CH_3 | -CH_2-(2,3,6-trichlorophenyl) | |
| 2.48 | H | CH_3 | CH_3-CCl_2- | |
| 2.49 | H | CH_3 | 4-Cl-C_6H_4-OCH_2- | 155–157 |
| 2.50 | H | CH_3 | 2,4-diCl-C_6H_3-OCH_2- | |
| 2.51 | H | CH_3 | 4-Cl-2-CH_3-C_6H_3-OCH_2- | 173–176 |
| 2.52 | H | CH_3 | 2-CH_3-C_6H_4-OCH(CH_3)- | |
| 2.53 | H | CH_3 | 4-Cl-2-CH_3-C_6H_3-OCH(CH_3)- | |
| 2.54 | H | H | 4-Cl-2-CH_3-C_6H_3-OCH(CH_3)- | |

TABLE 2-continued
Compounds of formula III:
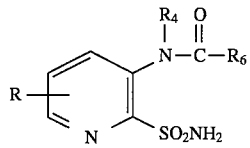
(III)
| Comp. No. | R | R₄ | R₆ | m.p. [°C.] |
|---|---|---|---|---|
| 2.55 | H | CH₃ | 4-Cl-2-CH₃-phenyl-O-CH(CH₃)- | |
| 2.56 | H | CH₃ | (CH₃)₂CH—O— | |
| 2.57 | H | CH₃ | CH₃—CH(C≡CH)—O— | |
| 2.58 | H | CH₃ | 3-(NHCOOCH₃)-phenyl-O- | |
| 2.59 | H | CH₃ | —O—N=C(CH₃)₂ | |
| 2.60 | H | H | —O—N=C(CH₃)₂ | |
| 2.61 | H | CH₃ | 2,6-di-C(CH₃)₃-phenyl-O- | |
| 2.62 | H | CH₃ | 3,4-di-Cl-phenyl-CH₂O- | |
| 2.63 | H | CH₃ | CH₂OCH₃ | 161–163 |

TABLE 3

Compounds of formula I:

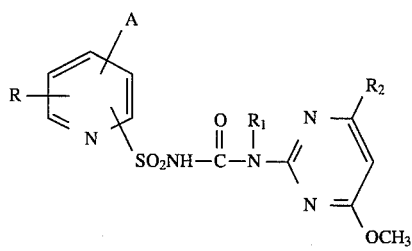

(I)

| Comp. No. | R | $R_1$ | $R_2$ | Pos. SO$_2$ | Pos. A | A | m.p. [°C] |
|---|---|---|---|---|---|---|---|
| 3.01 | H | H | OCH$_3$ | 2 | 3 | —OCH$_2$CH$_2$Cl | |
| 3.02 | H | H | CH$_3$ | 2 | 3 | —OCHF$_2$ | |
| 3.03 | H | H | OCH$_3$ | 2 | 3 | —SO$_2$CH$_2$CH$_3$ | |
| 3.04 | H | H | OCH$_3$ | 2 | 3 | —N(CH$_3$)—C(O)—CH$_3$ | |

TABLE 4

Compounds of formula XIa:

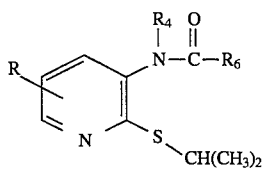

(XIa)

| Comp. No. | R | $R_4$ | $R_6$ | m.p. [°C] |
|---|---|---|---|---|
| 4.01 | H | CH$_3$ | CH$_3$ | 51–52 |
| 4.02 | H | CH$_3$ | phenyl | 86–87 |
| 4.03 | H | CH$_3$ | CHCl$_2$ | 105–107 |
| 4.04 | H | CH$_3$ | CH$_2$OCH$_3$ | 82–83 |
| 4.05 | H | H | H | |
| 4.06 | H | H | CH$_3$ | |
| 4.07 | H | CH$_3$ | H | $n_D^{22}$: 1.5582 |
| 4.08 | 6-CH$_3$ | CH$_3$ | CH$_3$ | |

Biological Examples

Example B 1: Postemergence phytotoxic action of the herbicides of formula I and of the mixtures of herbicide and safener of formula II on maize Maize is grown under greenhouse conditions in plastics pots to the 2.5 leaf stage. At that stage, a herbicide of formula I alone and also a mixture of the herbicide and safeners of formula II are applied to the test plants. Application is in the form of an aqueous suspension of the test compounds in 500 l water/ha. The rates of application for the herbicide are 125/60/30/15/8 and 250/125/60 g/ha, respectively, and the rates of application for the safener are 60 g/ha. Evaluation is made 23 days after the application using a scale of percentages. 100% indicates that the test plant has withered, 0% indicates no phytotoxic action. The results show that the safeners used can significantly reduce the damage caused to maize by the herbicide. Examples of the good protective activity of the safeners are given in Table B1.

TABLE B1

| Herbicide Comp. No. | Safener, g/ha | Herbicide concentration g/ha | | | | | |
|---|---|---|---|---|---|---|---|
| | | 250 | 125 | 60 | 30 | 15 | 8 |
| 3.04 | — | | 95 | 90 | 90 | 70 | 65 |
| 3.04 | IIb 60 | | 5 | 0 | 0 | 0 | 0 |
| 3.03 | — | 90 | 80 | 70 | | | |
| 3.03 | IIb 60 | 50 | 30 | 10 | | | |

Example B2: Use of a mixture of herbicide of formula I and safener of formula II for dressing maize seed Maize seed is dressed with a safener in an amount corresponding to 1 g/kg seed. The maize is then grown under greenhouse conditions in plastics pots to the 2.5 leaf stage. In parallel with the treated maize, untreated maize is cultivated to the same stage. At that stage the herbicide of formula I is applied to treated and untreated test plants. Application is in the form of an aqueous suspension of the herbicide in 500 l water/ha. The rate of application for the herbicide is 125, 60, 30, 15 and 250/125/60 g/ha, respectively, and the rate of application for the seed-dressing safener of formula II is 1 g/kg seed. Evaluation is made 14 days after the application using a scale of percentages. 100% indicates that the test plant has withered, 0% indicates no phytotoxic action. The results show that the safener as a seed-dressing agent significantly reduces the damage caused by the herbicide postemergence. Similar results are obtained when the herbicide is applied preemergence. Examples of the good activity of the safeners of formula II are shown in Table B2:

TABLE B2

| Herbicide Comp. No. | Safener, g/kg seed | Herbicide concentration g/ha | | | | |
|---|---|---|---|---|---|---|
| | | 250 | 125 | 60 | 30 | 15 |
| 3.04 | — | | | 90 | 80 | 50 |
| 3.04 | IIa 1 | | | 10 | 10 | 10 |
| 3.02 | — | | | 100 | 95 | 95 |
| 3.02 | IIa 1 | | | 65 | 50 | 25 |
| 3.03 | — | 90 | 80 | 70 | | |
| 3.03 | IIa 1 | 0 | 0 | 0 | | |

Example B3: Postemergence phytotoxic action of the herbicides of formula I and of the mixtures of herbicide and safener of formula II in sugar cane Sugar cane is grown under greenhouse conditions in plastics pots to the 3-leaf stage. At that stage, a herbicide of formula I alone and also a mixture of the herbicide and safeners of formula II are applied to the test plants. Application is in the form of an aqueous suspension of the test compounds in 500 l water/ha. The rates of application for the herbicide are 120/60/30 g/ha and the rates of application for the safener are 60 g/ha.

Evaluation is made 21 days after application using a scale of percentages. 100% indicates that the test plant has withered, 0% indicates no phytotoxic action. The results show that the safeners used can significantly reduce the damage caused to sugar cane by the herbicide. Examples of the good protective activity of the safeners are given in Table B3:

TABLE B3

| Herbicide Comp. No. | Safener, g/ha | | Herbicide concentration g/ha | | |
|---|---|---|---|---|---|
| | | | 120 | 60 | 30 |
| 1.01 | — | | 50 | 30 | 15 |
| 1.01 | IIb | 60 | 30 | 0 | 0 |
| 1.01 | IIc | 60 | 25 | 5 | 0 |

Example B4: Preemergence herbicidal action

Plastics pots are filled with expanded vermiculite. The test compounds are then applied in such a manner that the final concentration in the nutrient medium is 70 ppm. The seeds of monocotyledonous and dicotyledonous test plants are then sown and cultivated in a climatic chamber under optimum conditions. Evaluation is made 10 days later using a scale of nine ratings (1=complete destruction, 9=no activity). Ratings from 1 to 4 (especially from 1 to 3) indicate good to very good herbicidal activity. Examples of the good herbicidal activity of the compounds of formula Ib are given in Table B4:

TABLE B4

Preemergence action of herbicides of formula Ib:
Concentration of the test compound emulsion: 70 ppm

| Test plant: Compound No. | Nasturtium | Agrostis | Stellaria | Digitaria |
|---|---|---|---|---|
| 1.01 | 2 | 2 | 2 | 2 |
| 1.02 | 3 | 3 | 3 | 3 |
| 1.03 | 3 | 3 | 2 | 2 |
| 1.04 | 3 | 3 | 3 | 3 |
| 1.31 | 3 | 3 | 3 | 3 |
| 1.33 | 3 | 3 | 3 | 3 |
| 1.40 | 3 | 3 | 2 | 2 |
| 1.45 | 3 | 3 | 3 | 4 |
| 1.60 | 3 | 3 | 3 | 3 |
| 1.63 | 3 | 3 | 3 | 2 |
| 1.69 | 3 | 3 | 3 | 4 |
| 1.80 | 3 | 3 | 3 | 3 |
| 1.97 | 3 | 3 | 3 | 3 |
| 1.98 | 4 | 3 | 3 | 3 |
| 1.100 | 3 | 3 | 3 | 3 |
| 1.101 | 3 | 3 | 3 | 2 |

Formulation Examples for compounds of formula II or mixtures of the same with a herbicide of formula I (throughout, percentages are by weight)

| 1. Emulsifiable concentrates | a) | b) | c) |
|---|---|---|---|
| compound mixture | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| compound mixture | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3. Granules | a) | b) |
|---|---|---|
| compound mixture | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | a) | b) |
|---|---|---|
| compound mixture | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 5. Wettable powders | a) | b) | c) |
|---|---|---|---|
| compound mixture | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | |
|---|---|
| compound mixture | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| compound mixture | 5% | 8% |

-continued

| 7. Dusts | a) | b) |
|---|---|---|
| talcum | 95% | — |
| kaolin | — | 92% |

Ready-for-use dusts are obtained by mixing the active ingredient with the carriers and grinding the mixture in a suitable mill.

| 8. Extruder granules | |
|---|---|
| compound mixture | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granules | |
|---|---|
| compound mixture | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrates | |
|---|---|
| compound mixture | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

What is claimed is:

1. A composition for the selective control of weeds in crops of useful plants, which comprises, as active ingredient, together with inert carriers and adjuvants, a mixture comprising a) a herbicidally effective amount of a pyridylsulfonylurea of formula I

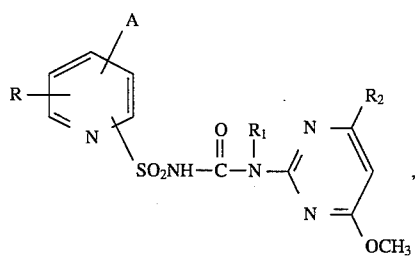

(I)

wherein R is hydrogen, halogen, $C_1$–$C_4$alkyl, $C_1$–$C_4$alkoxy or $C_1$–$C_4$alkylthio, or is $C_1$–$C_4$alkyl mono- or poly-substituted by halogen; $R_1$ is hydrogen or methyl; $R_2$ is methyl or methoxy; A is —X—$R_3$ or —N—($R_4$)$R_5$; $R_3$ is $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_3$–$C_6$cycloalkyl, which may for its part be interrupted by oxygen; or is $C_3$–$C_6$alkenyl, or $C_3$–$C_6$alkenyl that is mono- or poly-substituted by halogen, $C_1$–$C_6$alkoxy, $C_3$–$C_6$alkenyloxy or by $C_3$–$C_6$alkynyloxy; or is $C_4$–$C_6$cycloalkyl, or $C_4$–$C_6$cycloalkyl that is mono- or poly-substituted by halogen or by $C_1$–$C_6$alkoxy; or is $C_3$–$C_6$cycloalkyl that is interrupted by oxygen; or is $C_3$–$C_6$alkynyl; X is oxygen or $S(O)_n$; n is 0, 1 or 2; $R_4$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio; $R_5$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio, or is $C(O)R_6$; and $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen; or is phenyl, benzyl, naphthyl or $OR_{12}$, or phenyl, benzyl or naphthyl each substituted by halogen, $C_1$–$C_4$alkyl, $C_1$–$C_4$haloalkyl, $C_1$–$C_4$alkoxy, $C_1$–$C_4$haloalkoxy, $C_3$–$C_6$alkenyloxy, $C_3$–$C_6$alkynyloxy, nitro, cyano, $COOR_{13}$, $NR_{15}R_{16}$, $C(O)NR_{17}R_{18}$, $X_1R_{20}$, $SO_2NR_{21}R_{22}$ or by $X_2R_{23}$; $R_{12}$ is $C_1$–$C_6$alkyl, $C_1$–$C_6$haloalkyl, oxetan-3-yl, or $C_4$–$C_6$cycloalkyl, which may for its part be substituted by halogen, $C_1$–$C_4$alkyl or by $C_1$–$C_4$alkoxy; or is phenyl, benzyl or naphthyl, or phenyl, benzyl or naphthyl each substituted by $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$alkylsulfinyl, nitro, cyano, $COOR_{27}$, $NR_{25}R_{26}$, $CONR_{28}R_{29}$ or by $SO_2NR_{30}R_{14}$; or is $C_1$–$C_6$alkyl substituted by $C_1$–$C_4$alkoxy, $C_3$–$C_6$cycloalkyl, cyano, $COOR_{24}$ or by $CONR_{32}R_{33}$; or is $C_3$–$C_6$alkenyl, $C_3$–$C_6$haloalkenyl, $C_3$–$C_6$alkynyl, $C_3$–$C_6$haloalkynyl, $X_3R_{35}$ or $X_4R_{36}$; $R_{13}$ is hydrogen, $C_1$–$C_6$alkyl, $C_3$–$C_6$alkenyl, $C_3$–$C_6$alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ and $R25$ are each independently of the other the groups —C(O)—$X_5$—$C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_5$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_4$alkyl or $C_1$–$C_4$haloalkyl; $R_{23}$ and $R_{36}$ are each independently of the other $C_1$–$C_4$alkyl substituted by $COOR_{34}$; $R_{24}$, $R_{27}$ and $R_{34}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; and $R_{37}$ is hydrogen, $C_1$–$C_4$alkyl, $C_3$–$C_6$alkenyl or $C_3$–$C_6$alkynyl; or an N-oxide or a salt of a compound of formula I, and b) a herbicide-antagonistically effective amount of a sulfamoylphenylurea of formula II

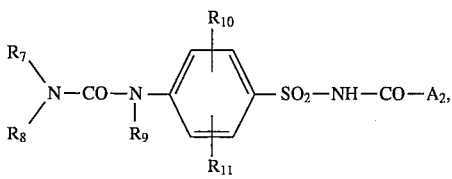 (II)

wherein $A_2$ is a radical from the group

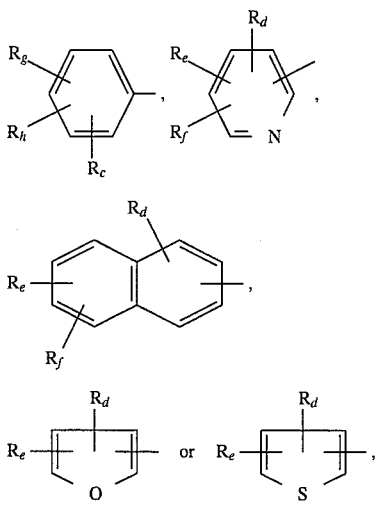

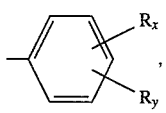 or 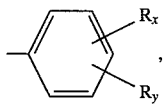, $R_7$ and $R_8$ are each independently of the other hydrogen, $C_1$–$C_8$alkyl, $C_3$–$C_8$cycloalkyl, $C_3$–$C_6$alkenyl, $C_3$–$C_6$alkynyl or

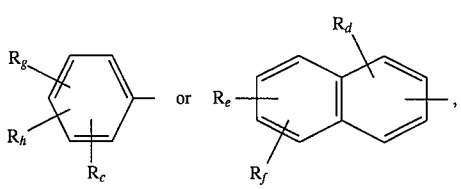

or are $C_1$–$C_4$alkyl substituted by $C_1$–$C_4$alkoxy or by

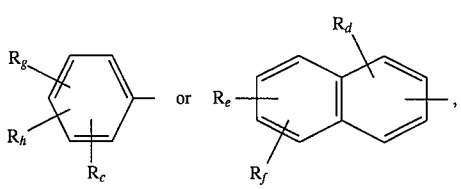, $R_7$ and $R_8$ together form a $C_4$–$C_6$alkylene bridge, or a $C_4$–$C_6$alkylene bridge interrupted by oxygen, sulfur, SO, $SO_2$, NH or by —N($C_1$–$C_4$alkyl)—; $R_9$ is hydrogen or $C_1$–$C_4$alkyl; $R_{10}$ and $R_{11}$ are each independently of the other hydrogen, halogen, cyano, nitro, trifluoromethyl, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$, CONR$_k$R$_m$, —COR$_n$, —SO$_2$NR$_k$R$_m$ or —OSO$_2$—$C_1$–$C_4$alkyl; or $R_{10}$ and $R_{11}$ together form a $C_3$–$C_4$alkylene bridge, which may be substituted by halogen or by $C_1$–$C_4$alkyl, or a $C_3$–$C_4$alkenylene bridge, which may be substituted by halogen or by $C_3$- or $C_4$-alkyl, or a butadienylene bridge, which may be substituted by halogen or by $C_1$–$C_4$alkyl, and $R_g$ and $R_h$ are each independently of the other hydrogen, halogen, $C_1$–$C_4$alkyl, trifluoromethyl, methoxy, methylthio or —COOR$_j$; $R_c$ is hydrogen, halogen, $C_1$–$C_4$alkyl or methoxy; $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$ or —CONR$_k$R$_m$; and $R_e$ is hydrogen, halogen, halo-$C_1$–$C_4$alkyl, $C_1$–$C_4$alkyl, —COOR$_j$, trifluoromethyl or methoxy; or $R_d$ and $R_e$ together form a $C_3$–$C_4$alkylene bridge; $R_f$ is hydrogen, halogen or $C_1$–$C_4$alkyl; $R_x$ and $R_y$ are each independently of the other hydrogen, halogen, $C_1$–$C_4$alkyl, $C_1$–$C_4$alkoxy, $C_1$–$C_4$alkylthio, —COOR$_{17}$, trifluoromethyl, nitro or cyano; $R_{17}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy; or is furoyl or thienyl; or is $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$ alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl or by di-$C_1$–$C_4$alkylaminocarbonyl; or is phenylaminocarbonyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy or that is mono-substituted in the phenyl ring by cyano or by nitro; or is dioxolan-2-yl that is unsubstituted or substituted by one or two $C_1$–$C_4$alkyl radicals; or is dioxan-2-yl that is unsubstituted or substituted by one or two $C_1$–$C_4$alkyl radicals; or is $C_1$–$C_4$alkyl that is substituted by cyano, nitro, carboxy or by $C_1$–$C_8$ alkylthio-$C_1$–$C_8$alkoxycarbonyl; $R_j$, $R_k$ and $R_m$ are each independently of the others hydrogen or $C_1$–$C_4$alkyl; or $R_k$ and $R_m$ together form a $C_4$–$C_6$alkylene bridge, or a $C_4$–$C_6$alkylene bridge interrupted by oxygen, NH or by —N($C_1$–$C_4$alkyl)—; and $R_n$ is $C_1$–$C_4$alkyl, phenyl, or phenyl substituted by halogen, $C_1$–$C_4$alkyl, methoxy, nitro or by trifluoromethyl; or a salt of a compound of formula II.

2. A composition according to claim 1, wherein $R_6$ is hydrogen, $C_1$–$C_6$alkyl or $C_3$–$C_6$cycloalkyl.

3. A composition according to claim 1, wherein $R_3$ is $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_3$–$C_6$cycloalkyl, which may for its part be interrupted by oxygen; or is $C_3$–$C_6$alkenyl, or $C_3$–$C_6$alkenyl that is mono- or poly-substituted by halogen, $C_1$–$C_6$alkoxy, $C_3$–$C_6$alkenyloxy or by $C_3$–$C_6$alkynyloxy; or is $C_4$–$C_6$cycloalkyl, or $C_4$–$C_6$cycloalkyl that is mono- or poly-substituted by halogen or by $C_1$–$C_6$alkoxy or may be interrupted by oxygen; or is $C_3$–$C_6$alkynyl; and $R_6$ is hydrogen or $C_1$–$C_6$alkyl.

4. A composition according to claim 1, wherein $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen.

5. A composition according to claim 1, wherein, in the compound of formula II, $A_2$ is a radical of the formula wherein $R_g$ and $R_h$ are each independently of the other hydrogen, halogen, $C_1$–$C_4$alkyl, trifluoromethyl, methoxy, methylthio or COOR$_j$; $R_c$ is hydrogen, halogen, $C_1$–$C_4$alkyl or methoxy; $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$ or —CONR$_k$R$_m$; and $R_e$ is hydrogen, halogen, $C_1$–$C_4$alkyl, —COOR$_j$, trifluoromethyl or methoxy; or $R_d$ and $R_e$ together form a $C_3$- or $C_4$-alkylene bridge; $R_f$ is hydrogen, halogen or $C_1$–$C_4$alkyl; $R_j$, $R_k$ and $R_m$ are each independently of the others hydrogen or $C_1$–$C_4$alkyl; or $R_k$ and $R_m$ together form a $C_4$–$C_6$alkylene bridge, or a $C_4$–$C_6$alkylene bridge interrupted by oxygen, NH or by —N($C_1$–$C_4$alkyl)—.

6. A composition according to claim 5, wherein, in the compound of formula II, $R_c$, $R_d$, $R_e$, $R_g$ and $R_h$ are each independently of the others hydrogen, $C_1$–$C_4$alkyl or methoxy.

7. A composition according to claim 1, wherein, in the compound of formula II, each of $R_{10}$ and $R_{11}$ is hydrogen.

8. A composition according to claim 1, wherein, in the compound of formula II, each of $R_9$, $R_{10}$ and $R_{11}$ is hydrogen.

9. A composition according to claim 1, wherein the pyridylsulfonylurea of formula I is a compound of formula Ia

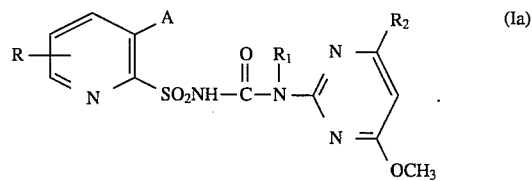

10. A composition according to claim 9, wherein R is hydrogen.

11. A composition according to claim 10, wherein each of R and $R_1$ is hydrogen and A is the group

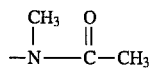

or —SO$_2$—$C_1$–$C_4$alkyl.

12. A composition according to claim 9, wherein A is —X—R$_3$.

13. A composition according to claim 9, wherein A is —N—(R$_4$)R$_5$.

14. A composition according to claim 9, wherein $R_5$ is C(O)R$_6$.

15. A composition according to claim 9, wherein each of R and $R_1$ is hydrogen and A is difluoromethoxy or the group

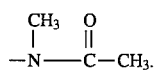

16. A composition according to claim 9, wherein the sulfamoylphenylurea of formula II is a compound of formula IIf

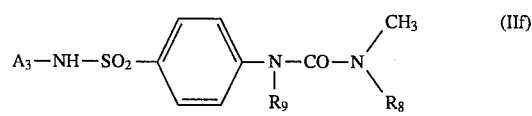

and $A_3$ is the group

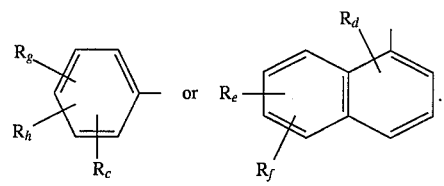

17. A composition according to claim 16, wherein, in the compound of formula IIf, each of $R_8$ and $R_9$ is hydrogen or methyl.

18. A composition according to claim 9, which comprises as compound of formula II a compound of formula IIa

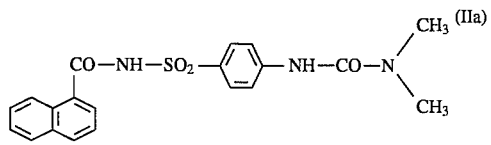

or of formula IIb

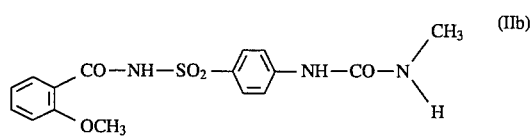

or of formula IIc

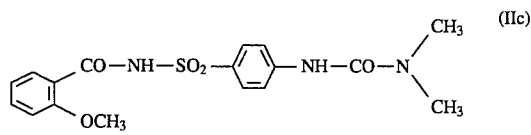

or of formula IId

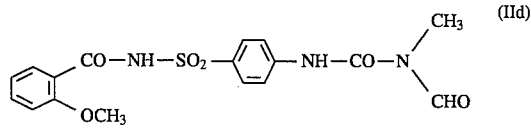

or of formula IIe

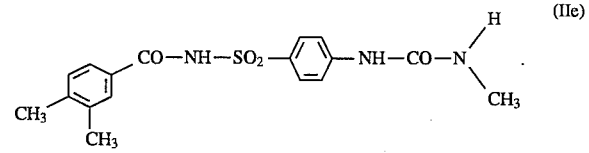

19. A compound of the formula Ib

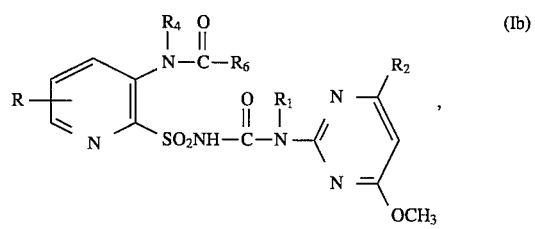

wherein R is hydrogen, halogen, $C_1$–$C_4$alkyl, $C_1$–$C_4$alkoxy or $C_1$–$C_4$alkylthio, or is $C_1$–$C_4$alkyl mono- or poly-substituted by halogen; $R_1$ is hydrogen or methyl; $R_2$ is methyl or methoxy; $R_4$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio; $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen; or is phenyl, benzyl, naphthyl or $OR_{12}$, or phenyl, benzyl or naphthyl each substituted by halogen, $C_1$–$C_4$alkyl, $C_1$–$C_4$haloalkyl, $C_1$–$C_4$alkoxy, $C_1$–$C_4$haloalkoxy, $C_3$–$C_6$alkenyloxy, $C_3$–$C_6$alkynyloxy, nitro, cyano, $COOR_{13}$, $NR_{15}R_{16}$, $C(O)NR_{17}R_{18}$, $X_1R_{20}$, $SO_2NR_{21}R_{22}$ or by $X_2R_{23}$; $R_{12}$ is $C_1$–$C_6$alkyl, $C_1$–$C_6$haloalkyl, oxetan-3-yl, or $C_4$–$C_6$cycloalkyl, which may for its part be substituted by halogen, $C_1$–$C_4$alkyl or by $C_1$–$C_4$alkoxy; or is phenyl, benzyl or naphthyl, or phenyl, benzyl or naphthyl each substituted by $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$alkylsulfinyl, nitro, cyano, $COOR_{27}$, $NR_{25}R_{26}$, $CONR_{28}R_{29}$ or by $SO_2NR_{30}R_{14}$; or is $C_1$–$C_6$alkyl substituted by $C_1$–$C_4$alkoxy, $C_3$–$C_6$cycloalkyl, cyano, $COOR_{24}$ or by $CONR_{32}R_{33}$; or is $C_3$–$C_6$alkenyl, $C_3$–$C_6$haloalkenyl, $C_3$–$C_6$alkynyl, $C_3$–$C_6$haloalkynyl, $X_3R_{35}$ or $X_4R_{36}$; $R_{13}$ is hydrogen, $C_1$–$C_6$alkyl, $C_3$–$C_6$alkenyl, $C_3$–$C_6$alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ and $R_{25}$ are each independently of the other the groups —C(O)—$X_5$—$C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_5$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_4$alkyl or $C_1$–$C_4$haloalkyl; $R_{23}$ and $R_{36}$ are each independently of the other $C_1$–$C_4$alkyl substituted by $COOR_{34}$; $R_{24}$, $R_{27}$ and $R_{34}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; and $R_{37}$ is hydrogen, $C_1$–$C_4$alkyl, $C_3$–$C_6$alkenyl or $C_3$–$C_6$alkynyl.

20. A compound according to claim 19, wherein $R_6$ is hydrogen or $C_1$–$C_6$alkyl.

21. A method of selectively controlling weeds and grasses in crops of useful plants, which comprises treating the crops, their seed or the crop area thereof with an effective amount of a pyridylsulfonylurea herbicide of formula I

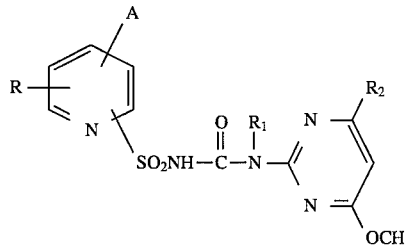

or an N-oxide or a salt thereof, and a herbicide-antagonistically effective amount of a sulfamoylphenylurea compound of formula II

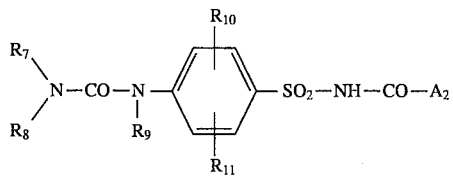

or a salt thereof, simultaneously or independently of one another, wherein R is hydrogen, halogen, $C_1$–$C_4$alkyl, $C_1$–$C_4$alkoxy or $C_1$–$C_4$alkylthio, or is $C_1$–$C_4$alkyl mono- or poly-substituted by halogen; $R_1$ is hydrogen or methyl; $R_2$ is methyl or methoxy; A is —X—$R_3$ or —N—$(R_4)R_5$; $R_3$ is $C_1$–$C_6$alkyl, or $C_1$–$C_6$alkyl that is mono- or poly-substituted by halogen, $C_1$–$C_6$alkoxy, $C_3$–$C_6$-alkenyloxy $C_3$–$C_6$alkynyloxy or by $C_3$–$C_6$cycloalkyl, which may for its part be interrupted by oxygen; or is $C_3$–$C_6$alkenyl, or $C_3$–$C_6$alkenyl that is mono- or poly-substituted by halogen, $C_1$–$C_6$alkoxy, $C_3$–$C_6$alkenyloxy or by $C_3$–$C_6$alkynyloxy; or is $C_4$–$C_6$cycloalkyl, or $C_4$–$C_6$cycloalkyl that is mono- or poly-substituted by halogen or by $C_1$–$C_6$alkoxy; or is $C_3$–$C_6$cycloalkyl that is interrupted by oxygen; or is $C_3$–$C_6$alkynyl; X is oxygen or $S(O)_n$; n is 0, 1 or 2; $R_4$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio; $R_5$ is hydrogen, $C_1$–$C_6$alkyl, or $C_1$–$C_6$alkyl that is mono- or poly-substituted by halogen, $C_1$–$C_6$alkoxy, $C_3$–$C_6$alkenyloxy, $C_3$–$C_6$alkynyloxy or by $C_1$–$C_6$alkylthio, or is $C(O)R_6$; and $R_6$ is hydrogen, $C_1$–$C_6$alkyl, $C_3$–$C_6$cycloalkyl or $C_2$–$C_6$alkynyl; or is $C_1$–$C_6$alkyl or $C_3$–$C_6$cycloalkyl each substituted by halogen or by $C_1$–$C_4$alkoxy; or is $C_2$–$C_6$alkenyl, or $C_2$–$C_6$alkenyl substituted by halogen; or is phenyl, benzyl, naphthyl or $OR_{12}$, or phenyl, benzyl or naphthyl each substituted by halogen, $C_1$–$C_4$alkyl, $C_1$–$C_4$haloalkyl, $C_1$–$C_4$alkoxy, $C_1$–$C_4$haloalkoxy, $C_3$–$C_6$alkenyloxy, $C_3$–$C_6$alkynyloxy, nitro, cyano, $COOR_{13}$, $NR_{15}R_{16}$, $C(O)NR_{17}R_{18}$, $X_1R_{20}$, $SO_2NR_{21}R_{22}$ or by $X_2R_{23}$; $R_{12}$ is $C_1$–$C_6$alkyl, $C_1$–$C_6$haloalkyl, oxetan-3-yl, or $C_4$–$C_6$cycloalkyl, which may for its part be substituted by halogen, $C_1$–$C_4$alkyl or by $C_1$–$C_4$alkoxy; or is phenyl, benzyl or naphthyl, or phenyl, benzyl or naphthyl each substituted by $C_1$–$C_4$alkyl, $C_1$–$C_6$haloalkyl, $C_1$–$C_4$alkoxy, $C_1$–$C_4$haloalkoxy, $C_1$–$C_4$ $C_1$–$C_4$haloalkylthio, $C_1$–$C_4$alkylsulfonyl, $C_1$–$C_4$alkylsulfinyl, nitro, cyano, $COOR_{27}$, $NR_{25}R_{26}$, $CONR_{28}R_{29}$ or by $SO_2NR_{30}R_{14}$; or is $C_1$–$C_6$alkyl substituted by $C_1$–$C_4$alkoxy, $C_3$–$C_6$-cycloalkyl cyano, $COOR_{24}$ or by $CONR_{32}R_{33}$; or is $C_3$–$C_6$alkenyl, $C_3$–$C_6$haloalkenyl, $C_3$–$C_6$alkynyl, $C_3$–$C_6$haloalkynyl, $X_3R_{35}$ or $X_4R_{36}$; $R_{13}$ is hydrogen, $C_1$–$C_6$alkyl, $C_3$–$C_6$alkenyl, $C_3$–$C_6$alkynyl or oxetan-3-yl; $R_{14}$, $R_{15}$, $R_{16}$, $R_{17}$, $R_{18}$, $R_{21}$, $R_{22}$, $R_{25}$, $R_{26}$, $R_{28}$, $R_{29}$, $R_{30}$, $R_{32}$ and $R_{33}$ are each independently of the others hydrogen, $C_1$–$C_4$alkyl, $C_3$–$C_6$alkenyl or $C_3$–$C_6$alkynyl; or $R_{15}$ and $R_{25}$ are each independently of the other the groups —C(O)—$X_5$—$C_1$–$C_4$alkyl or —C(O)—$C_1$–$C_4$alkyl, which may for their part be substituted by halogen; or $R_{15}$ and $R_{16}$ or $R_{17}$ and $R_{18}$ or $R_{21}$ and $R_{22}$ or $R_{25}$ and $R_{26}$ or $R_{28}$ and $R_{29}$ or $R_{30}$ and $R_{14}$ or $R_{32}$ and $R_{33}$ together form a $C_4$–$C_8$alkylene chain, which may for its part be interrupted by oxygen or by $NR_{19}$, $R_{19}$ is hydrogen, $C_1$–$C_4$alkyl, $C_3$–$C_6$alkenyl or $C_3$–$C_6$alkynyl; $R_{20}$ and $R_{35}$ are each independently of the other $C_1$–$C_6$alkyl or $C_1$–$C_4$haloalkyl; $R_{23}$ and $R_{36}$ are each independently of the other $C_1$–$C_4$alkyl substituted by $COOR_{34}$; $R_{24}$, $R_{27}$ and $R_{34}$ are each independently of the other hydrogen or $C_1$–$C_4$alkyl; $X_1$ and $X_3$ are each independently of the other sulfur, SO or $SO_2$; $X_2$ and $X_4$ are each independently of the other oxygen or sulfur; $X_5$ is oxygen or $NR_{37}$; $R_{37}$ is hydrogen, $C_1$–$C_4$alkyl, $C_3$–$C_6$alkenyl or $C_3$–$C_6$alkynyl; $A_2$ is a radical from the group

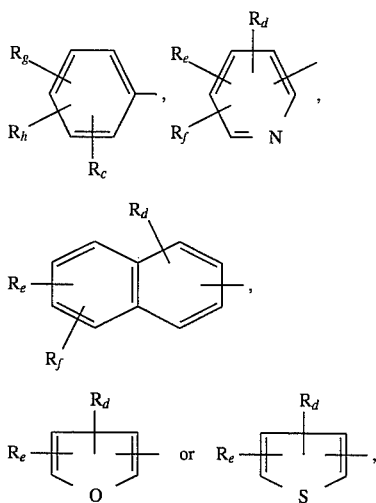

$R_7$ and $R_8$ are each independently of the other hydrogen, $C_1$–$C_8$alkyl, $C_3$–$C_8$cycloalkyl, $C_3$–$C_6$alkenyl, $C_3$–$C_6$alkynyl or

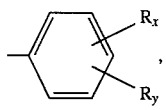

or are $C_1$–$C_4$alkyl substituted by $C_1$–$C_4$alkoxy or by

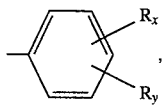

$R_7$ and $R_8$ together form a $C_4$–$C_6$alkylene bridge, or a $C_4$–$C_6$alkylene bridge interrupted by oxygen, sulfur, SO, $SO_2$, NH or by —N($C_1$–$C_4$alkyl)—; $R_9$ is hydrogen or $C_1$–$C_4$alkyl; $R_{10}$ and $R_{11}$ are each independently of the other hydrogen, halogen, cyano, nitro, trifluoromethyl, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$, —$CONR_kR_m$, —$COR_n$, —$SO_2NR_kR_m$ or —$OSO_2$–$C_1$–$C_4$alkyl; or $R_{10}$ and $R_{11}$ together form a $C_3$–$C_4$alkylene bridge, which may be substituted by halogen or by $C_1$–$C_4$alkyl, or a $C_3$–$C_4$alkenylene bridge, which may be substituted by halogen or by $C_3$– or $C_4$-alkyl, or a butadienylene bridge, which may be substituted by halogen or by $C_1$–$C_4$alkyl, and $R_g$ and $R_h$ are each independently of the other hydrogen, halogen, $C_1$–$C_4$alkyl, trifluoromethyl, methoxy, methylthio or —CO-$OR_j$; $R_c$ is hydrogen, halogen, $C_1$–$C_4$alkyl or methoxy; $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or —$CONR_kR_m$; and $R_e$ is hydrogen, halogen, halo-$C_1$–$C_4$alkyl, $C_1$–$C_4$alkyl, —$COOR_j$, trifluoromethyl or methoxy; or $R_d$ and $R_e$ together form a $C_3$–$C_4$alkylene bridge; $R_f$ is hydrogen, halogen or $C_1$–$C_4$alkyl; $R_x$ and $R_y$ are each independently of the other hydrogen, halogen, $C_1$–$C_4$alkyl, $C_1$–$C_4$alkoxy, $C_1$–$C_4$alkylthio, —$COOR_{17}$, trifluoromethyl, nitro or cyano; $R_{17}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy; or is furoyl or thienyl; or is $C_1$–$C_4$alkyl substituted by phenyl, halophenyl, $C_1$–$C_4$alkylphenyl, $C_1$–$C_4$-alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl or by di-$C_1$–$C_4$alkylaminocarbonyl; or is phenylaminocarbonyl that is unsubstituted or mono- to tri-substituted in the phenyl ring by the same or different substituents selected from halogen, $C_1$–$C_4$alkyl, halo-$C_1$–$C_4$alkyl, halo-$C_1$–$C_4$alkoxy and $C_1$–$C_4$alkoxy or that is mono-substitute in the phenyl ring by cyano or by nitro; or is dioxolan-2-yl that is unsubstituted or substituted by one or two $C_1$–$C_4$alkyl radicals; or is dioxan-2-yl that is unsubstituted or substituted by one or two $C_1$–$C_4$alkyl radicals; or is $C_1$–$C_4$alkyl that is substituted by cyano, nitro, carboxy or by $C_1$–$C_8$alkylthio-$C_1$–$C_8$alkoxycarbonyl; $R_j$, $R_k$ and $R_m$ are each independently of the others hydrogen or $C_1$–$C_4$alkyl; or $R_k$ and $R_m$ together form a $C_4$–$C_6$alkylene bridge, or a $C_4$–$C_6$alkylene bridge interrupted by oxygen, NH or by —N($C_1$–$C_4$alkyl)—; and $R_n$ is $C_1$–$C_4$alkyl, phenyl, or phenyl substituted by halogen, $C_1$–$C_4$alkyl, methoxy, nitro or by trifluoromethyl.

22. A method according to claim 21, wherein the crops or the crop area is treated with from 0.001 to 2 kg/ha of the pyridylsulfonylurea herbicide of formula I or the N-oxide or salt thereof and from 0.005 to 0.5 kg/ha of the sulfamoylphenylurea compound of formula II or the salt thereof.

23. A method according to claim 21 wherein the crops of useful plants are maize or sugar cane.

* * * * *

Adverse Decisions In Interference

Patent No. 5,532,203, Werner Fory, Elmar Kerber, Manfred Hudetz, SELECTIVE SAFENED HERBICIDAL COMPOSITION, Interference No. 104,080, final judgment adverse to the patentees rendered August 19, 1998, as to claims 19 and 20.

*(Official Gazette October 27, 1998)*